United States Patent
Rosenzweig et al.

(10) Patent No.: US 10,456,398 B2
(45) Date of Patent: *Oct. 29, 2019

(54) INHIBITION OF SGK1 IN THE TREATMENT OF HEART CONDITIONS

(71) Applicant: Beth Israel Deaconess Medical Center, Inc., Boston, MA (US)

(72) Inventors: Anthony Rosenzweig, Newton, MA (US); Saumya Das, Lexington, MA (US); Alan C. Rigby, Newton, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/891,626

(22) Filed: Feb. 8, 2018

(65) Prior Publication Data

US 2018/0243301 A1 Aug. 30, 2018

Related U.S. Application Data

(63) Continuation of application No. 15/024,943, filed as application No. PCT/US2014/057839 on Sep. 26, 2014, now Pat. No. 9,974,788.

(60) Provisional application No. 61/882,946, filed on Sep. 26, 2013, provisional application No. 61/882,938, filed on Sep. 26, 2013, provisional application No. 61/883,117, filed on Sep. 26, 2013.

(51) Int. Cl.
*A61K 31/513* (2006.01)
*A61K 38/43* (2006.01)
*C07K 16/40* (2006.01)

(52) U.S. Cl.
CPC ............ *A61K 31/513* (2013.01); *A61K 38/43* (2013.01); *C07K 16/40* (2013.01); *C07K 2317/21* (2013.01); *C07K 2317/24* (2013.01); *C07K 2317/569* (2013.01); *C07K 2317/622* (2013.01); *C07K 2317/76* (2013.01)

(58) Field of Classification Search
CPC ............................. A61K 31/513; A61K 39/00
See application file for complete search history.

(56) References Cited

U.S. PATENT DOCUMENTS

2008/0015141 A1 1/2008 Lang et al.
2008/0262096 A1 10/2008 Mederski et al.

FOREIGN PATENT DOCUMENTS

WO 01/93841 A2 12/2001
WO 03/074497 A1 9/2003
WO 2013/041119 A1 3/2013

OTHER PUBLICATIONS

Seebohm et al. Long QT syndrome-associated mutations in KCNQ1 and KCNE1 subunits disrupt normal endosomal recycling of IKs channels. Circ Res. 103(12):1451-7 (2008).

*Primary Examiner* — San Ming R Hui
(74) *Attorney, Agent, or Firm* — McCarter & English, LLP

(57) ABSTRACT

The present invention relates to the treatment of acquired and genetic heart conditions in a subject by the inhibition of SGK1, including Long QT syndrome and cardiovascular disease, including dilated cardiomyopathy. Cardiovascular diseases treatable by SGK1 inhibition include heart failure, arrhythmia, ischemic injury, ischemic infarction, cardiac fibrosis, vascular proliferation, restenosis, dilated cardiomyopathy, and stent failure. The present invention also identifies selective inhibitors of SGK1. The method comprises administering to the subject a therapeutically effective amount of an inhibitor of SG.

9 Claims, 10 Drawing Sheets

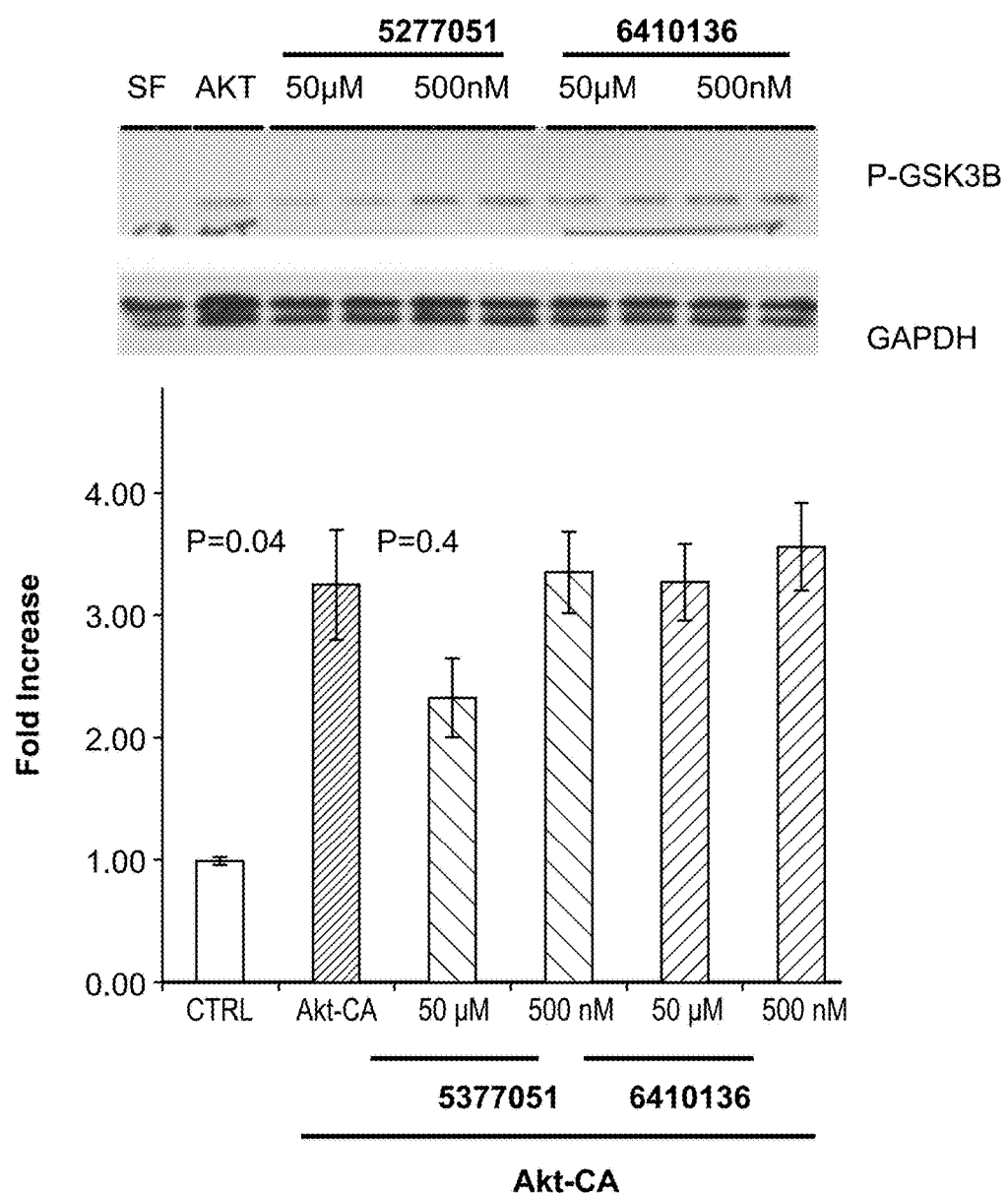

INHIBITION OF SGK1 IN THE TREATMENT OF HEART CONDITIONS

RELATED APPLICATIONS

This application is a Continuation of U.S. application Ser. No. 15/024,943, filed Mar. 25, 2016, which is a 35 U.S.C. § 371 national stage filing of International Application No. PCT/US2014/057839, filed on 26 Sep. 2014, which claims priority to Provisional Patent Application Ser. No. 61/882,938, filed on 26 Sep. 2013; Provisional Patent Application Ser. No. 61/882,946, filed on 26 Sep. 2013; and Provisional Patent Application Ser. No. 61/883,117, filed on 26 Sep. 2013; the entire contents of each of which are expressly incorporated herein by reference.

STATEMENT OF GOVERNMENT INTEREST

This invention was made with government support under HL094677 and HL104370 related by the NIH. The government has certain rights in the invention.

FIELD OF THE TECHNOLOGY

The present invention relates to treatment of heart conditions such as Long QT Syndrome and cardiovascular disease by inhibition of SGK1.

BACKGROUND

The annual incidence of sudden cardiac death in the United States is in the range of 180,000 to 250,000 per year and unlikely to subside in the future with the increase in the age of the population as well an increase in cardiac risk factors such as diabetes mellitus and obesity. Alterations in ionic fluxes comprise the cellular basis for the arrhythmias that underlie sudden arrhythmic deaths. These alterations usually lead to an increase in myocardial cell repolarization time and an increase in the duration of the action potential. This corresponds to an increase in the QT interval on a surface electrocardiogram. Prolongation in the QT interval has been noted in diverse conditions including myocardial ischemia, in response to administration of commonly used drugs such as erythromycin and haloperidol (as an unintended side-effect), and as a congenital condition.

Many genetic causes for long QT syndrome (LQTS) have been identified, with the majority of mutations seen in genes that encode for three main cardiac ion channels (KCNQ1, KCNH2 and SCN5a). Unfortunately there are no current therapies for the treatment of LQTS that address the underlying mechanistic problem, namely prolongation of the action potential and myocardial repolarization. Additionally, most anti-arrhythmic medications prolong myocardial repolarization and drugs that shorten QT interval are rare and have very small effects. Thus medications that alter ion channel function that lead to shortening of the action potential and myocardial repolarization would be a novel class of agents in treating patients with genetic and acquired LQTS.

Zebrafish recapitulate several key aspects of human myocardial repolarization and have a long history of being used successfully for high-throughput screening of drugs. Recently it was shown that zebrafish models of acquired LQTS as well as genetic LQTS can be used for screening small molecules that can shorten myocardial repolarization, thereby rescuing the zebrafish LQTS. In particular the breakdance (bkd) mutant carries a mutation in the KCNH2 gene with observed 2:1 heart block due to prolonged action potential and phenocopies human LQT2. High throughput screening for small molecules that rescue the phenotype of bkd has been successfully conducted.

In addition, cardiovascular disease is responsible for 600,000 deaths per year in the United States, making it the leading cause of death in both men and women. The total annual estimated costs associated with coronary artery disease alone amount to $109 billion.

Heart failure (HF) is a clinical syndrome of growing prevalence that can either be acquired, for example after myocardial infarction or pressure overload as in hypertension and valvular stenosis, or can be genetic due to de novo or inherited mutations. While there are evidence-based therapies for systolic HF, there has not been a new class of medications approved for HF in approximately a decade. Thus there is a substantial unmet clinical need for novel therapeutic approaches in HF.

Cardiomyopathies are a group of diseases affecting heart muscles, also known as the myocardium. Dilated cardiomyopathy weakens the heart and affects its ability to pump enough blood to the organs. This can lead to heart failure and death, as well as problems elsewhere in the body. Approximately 25-30% of heart failure may be due to genetic mutations that can occur de novo in affected individuals or can be familial and inherited. Although the genetic causes of dilated cardiomyopathy (DCM) are diverse, the most common genes affected encode structural components of the cytoskeleton and/or sarcomere. Treatment for dilated cardiomyopathy is limited, and includes drug treatment to alleviate symptoms, implantation of devices, and heart transplants. However these may have unwanted side effects or be ineffective. Accordingly, there is a need for further treatment options to deal with dilated cardiomyopathy.

SUMMARY

The present invention relates to the treatment of Long QT syndrome (genetic and acquired) and cardiovascular disease by the inhibition of SGK1. The present invention also identifies selective inhibitors of SGK1.

It has now been found that SGK1 inhibition in a zebrafish model of genetic, congenital Long QT syndrome has beneficial effects. The results given in Examples 2 and 3 show that SGK1 inhibition demonstrated significant rescue of the 2:1 AV block. Based on these discoveries, methods of treating Long QT Syndrome with SGK1 inhibitors are described herein.

In one aspect, the present invention is a method for treating a subject for long QT syndrome, comprising administering to the subject a therapeutically effective amount of an agent that inhibits SGK1. In some embodiments, the Long QT syndrome is genetic. In one or more embodiments, the genetic long QT syndrome is characterized by a mutation in the KCNQ1 gene, the KCNH2 gene, or the SCN5a gene. In some embodiments, the Long QT syndrome is acquired (for instance as a side effect of drugs such as erythromycin or haloperidol).

The present invention provides a number of advantages over current methods of treating Long QT syndrome (genetic and acquired). For instance, the present invention describes the unexpected observation that SGK1 inhibition can rescue the 2:1 phenotype in bkd (breakdance) mutants. The present invention also presents a new therapeutic target for Long QT syndrome.

Furthermore, it has now been found that SGK1 is persistently activated in a mouse model of pressure overload induced heart failure. The results given in Examples 2 and 3 show that genetic SGK1 inhibition mitigated the development of heart failure and fibrosis (scarring) after aortic constriction and reduced heart failure-associated biochemical changes in the sodium channel that lead to arrhythmia Based on these discoveries, methods of treating cardiovascular diseases with SGK1 inhibitors are described herein.

In another aspect, the invention is a method for treatment of a cardiovascular disease in a subject in need thereof. The method comprises administering to the subject a therapeutically effective amount of at least one SGK1 inhibitor. In one or more embodiments, the cardiovascular disease is selected from the group consisting of heart failure, arrhythmia, ischemic injury, ischemic infarction, cardiac fibrosis, vascular proliferation, restenosis, dilated cardiomyopathy, and stent failure. Suitable SGK1 inhibitors include: a small molecule compound; an anti-SGK1 antibody, or antigen-binding fragment thereof; a polypeptide decoy; a peptidomimetic; a peptide that inhibits the function of SGK1; a miRNA; an siRNA; an shRNA; a dsRNA; an antisense RNA directed to SGK1 DNA or RNA; or a polynucleotide encoding any of the above inhibitors.

It has also now been found that SGK1 is activated in hearts of patients with DCM (see Example 6). It has also been found that SGK1 inhibition in a murine model of human genetic DCM due to a mutation in the myosin heavy chain (MHC-F764L) mitigates the development of genetic DCM. Based on these discoveries, methods for treating a subject with dilated cardiomyopathy with SGK1 inhibitors are disclosed.

In another aspect, the present invention is a method for treating a subject for dilated cardiomyopathy (DCM) (genetic or acquired), comprising administering to the subject a therapeutically effective amount of an agent that inhibits SGK1. For example, the genetic dilated cardiomyopathy is characterized by a mutation in the MYH6 gene, the MYH7 gene, or the SCN5A gene. Alternatively, the cardiomyopathy is characterized by a mutation listed in Table 1 shown below in the "Detailed Description".

The present invention provides a number of advantages over current methods of treating HF, including dilated cardiomyopathy. For instance, the present invention describes the unexpected observation that SGK1 inhibition can have a protective effect on cardiac cells. The present invention also describes the observation that SGK1 is activated in human dilated cardiomyopathy, and that inhibition of SGK1 mitigates the effects of dilated cardiomyopathy. The present invention presents a new therapeutic target for cardiovascular disease.

BRIEF DESCRIPTION OF THE DRAWINGS

FIG. 7A Expression of constitutively active SGK1 (SGK1-CA) in HEK-Nav1.5 cells leads to increase in $I_{NA}$ density, while inhibition by expression of a dominant negative kinase dead form of SGK-1 (SGK1-DN) leads to decrease in $I_{NA}$ density ($*:p<0.05$ by one way ANOVA, n=7–11 for each condition); FIG. 7B Expression of SGK1-CA in HEK-Nav 1.5 cells leads to a hyperpolarizing shift of steady state activation and inactivation curves for $I_{NA}$; FIG. 7C Mutation of a novel SGK1 putative site T1590A leads to abrogation of the increase in $I_{NA}$ with SGK1 activation.

FIG. 8A-C show graphs regarding inhibition of SGK1 in cultured cardiomyocytes by lead compounds as follows: FIG. 8A Inhibition of SGK1 activity assessed by GSK3-beta phosphorylation in CMs infected by Ad.SGK1-CA. Different concentrations of 5377051 were assessed at 48 hours after treatment with immunoblotting (left) and quantitated (right); FIG. 8B Effect of SGK1 inhibitors on Akt-induced phosphorylation of GSK3-beta in CMs infected by Ad.-myr-Akt was assessed by immunoblotting; FIG. 8C Comparison of potency of 10 micromolar compounds 5377051, 6410136 with the published inhibitor EMD63863.

DETAILED DESCRIPTION

Figure 1:
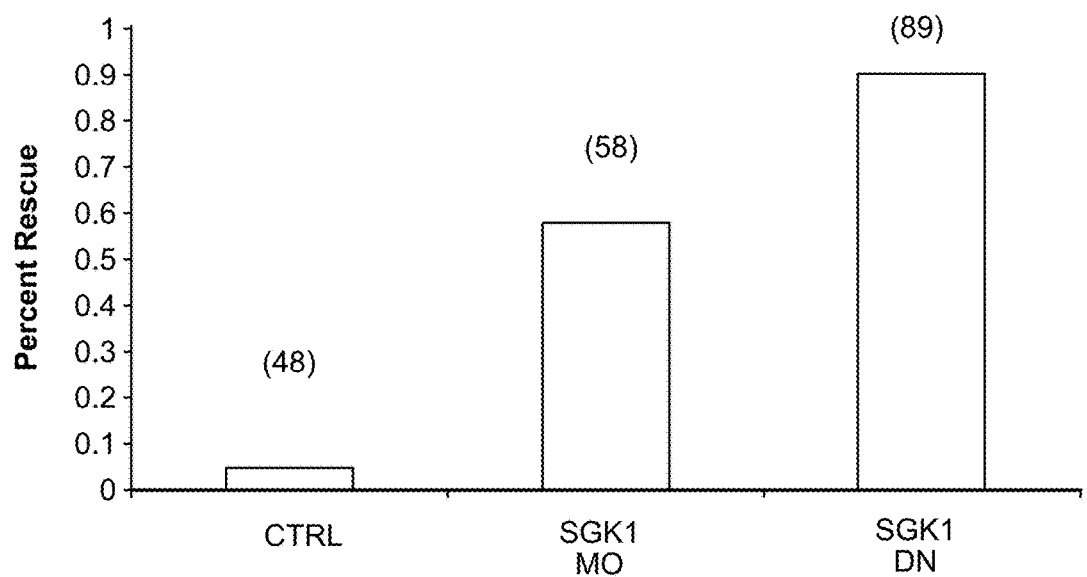
FIG. 1 shows the percent rescue of 2:1 AV block in bkd$^{-/-}$ mutant zebrafish treated with SGK1 morpholino (500 mM) or SGK1-DN mRNA (500 mM) at the 1-2 cell stage and scored for the phenotype at 99 hours post fertilization. The total number of fish are indicated above the corresponding columns.

The present invention relates to the treatment of Long QT syndrome (genetic or acquired), cardiovascular disease, (e.g., dilated cardiomyopathy (genetic or acquired) by the inhibition of SGK1. The present invention demonstrates that SGK1 inhibition in vivo has a protective effect and can alleviate symptoms associated with Long QT syndrome; can reduce and alleviate symptoms associated with heart failure, arrhythmia, ischemic injury, ischemic infarction, cardiac fibrosis, vascular proliferation, restenosis, genetic or acquired dilated cardiomyopathy, and stent failure.

Long QT Syndrome

Long QT syndrome can be genetic (e.g. caused by a mutation in the KCNQ1 gene, the KCNH2 gene, or the SCN5a gene). Alternatively, Long QT syndrome is not associated with a genetic mutation and is acquired as a result of exposure to an external stimulus. For instance, acquired Long QT syndrome can be a side effect of drugs such as erythromycin or haloperidol. Acquired Long QT syndrome is also associated with other heart conditions such as myocardial ischemia.

Dilated Cardiomyopathy

Genetic dilated cardiomyopathy is characterized by a mutation in any one of a number of genes. Below in Table 1 is given a list of genes that are known to be associated with genetic dilated cardiomyopathy. Table 1 is adapted from Hershberger et al. *J. Am. Coll. Cardiol.* 2011 Apr. 19; 57(16) 1641-1649. Genetic cardiomyopathies treatable by the disclosed invention, i.e., by SGK1 inhibition, include those characterized by a mutation listed in Table 1.

TABLE 1

Genes Associated with Genetic Dilated Cardiomyopathy

| Gene | Protein |
|---|---|
| LMNA | Lamin A/C |
| MYH6 | α-myosin heavy chain |
| MYH7 | β-myosin heavy chain |
| MYPN | Myopalladin |
| TNNT2 | Cardiac troponin T |
| SCN5A | Sodium channel |
| MYBPC3 | Myosin-binding protein C |
| RBM20 | RNA binding protein 20 |
| TMPO | Thymopoietin |
| LAMA4 | Laminin a-4 |
| VCL | Metavinculin |
| LDB3 | Cypher/ZASP |
| TCAP | Titin-cap or telethonin |
| PSEN1/2 | Presenilin 1/2 |
| ACTN2 | α-actinin-2 |
| CRYAB | Alpha B crystalin |
| TPM1 | α-tropomyosin |
| ABCC9 | SUR2A |
| ACTC | Cardiac actin |
| PDLIM3 | PDZ LIM domain protein 3 |
| ILK | Integrin-linked kinase |
| TNNC1 | Cardiac troponin C |
| PLN | Phospholamban |
| DES | Desmin |
| SGCD | δ-sarcoglycan |
| CSRP3 | Muscle LIM protein |
| TTN | Titin |
| EYA4 | Eyes-absent 4 |
| ANKRD1 | Ankyrin repeat domain containing protein 1 |
| DMD | Dystrophin |
| TAZ/G4.5 | tafazzin |

Acquired dilated cardiomyopathy refers to dilated cardiomyopathy having external or environmental causes and is not caused by genetic mutations. It is also something referred to as "heart failure."

SGK1

Serine/threonine-protein kinase (SGK1) (also known as serum/glucocorticoid-regulated kinase 1) is a protein kinase that plays a role in a cell's response to stress. In vivo, SGK1 activates certain potassium, sodium, and chloride channels. For instance, the protein is known to regulate the myo-inositol transporter during osmotic stress.

SGK1 Inhibitors

As used herein, the term "SGK1 inhibitor" refers to any agent that can block, arrest, interfere with, or reduce the biological activity of SGK1.

Inhibitors of SGK1 are known in the art, and can include small molecules. Although small molecules can have any molecular weight, they generally include molecules that are less than about 5,000 daltons.

For instance, small molecule SGK1 inhibitors are described in U.S. 2008/0262096 by Mederski et al. U.S. 2008/0262096 describes squaric acid compounds of the Formula (A), in which the variables R, $R^1$, $R^{1'}$, $R^2$ and X are defined in the specification as described below:

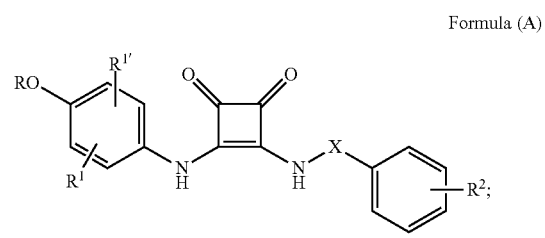

Formula (A)

in which
R denotes H or A,
$R^1$, $R^{1'}$ each, independently of one another, denote H, A, Hal, CN, $NO_2$, C(=O)A, CHO, CH(OH)A, $NH_2$, NH(C=O)A, COOH, COOA or $SO_2NH_2$, $CONH_2$ or $CONA_2$,
$R^2$ denotes OH, OA, Hal, $CF_3$, $NO_2$ or $SO_2NH_2$,
A denotes unbranched or branched alkyl having 1-10 C atoms, in which 1-7 H atoms may be replaced by F,
X is absent or denotes $CH_2$, CHA, $CA_2$ or

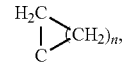

Hal denotes F, Cl, Br or I,
m denotes 0, 1 or 2, and
n denotes 1, 2, 3 or 4,
where bis(4-hydroxyphenylamino)cyclobut-3-ene-1,2-dione is excluded.

Small molecule SGK1 inhibitors have also been described in U.S. 2009/0221712 by Gericke et al. U.S. 2009/0221712 describes mandelic hydrazides of the Formula (B), in which the variables $R^1$-$R^{11}$ are defined in the specification as described below:

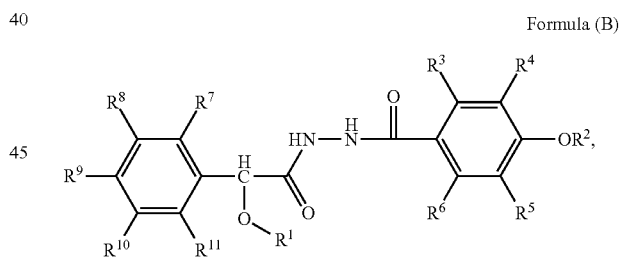

Formula (B)

in which
$R^1$, $R^2$ each, independently of one another, denote H, CHO or acetyl,
$R^3$, $R^4$, $R^5$, $R^6$, $R^7$, $R^8$, $R^9$, $R^{10}$, $R^{11}$ each, independently of one another, denote H, A, $OSO_2A$, Hal, $NO_2$, $OR^{12}$, $N(R^{12})_2$, CN, O—COA, —[C($R^{12})_2]_n COOR^{12}$, O—[C($R^{12})_2]_n COOR^{12}$, $SO_3H$, —[C($R^{12})_2]_n$Ar, —CO—Ar, O—[C($R^2)_2]_n$Ar, —[C($R^{12})_2]_n$Het, —[C($R^{12})_2]_n$C≡CH, O—[C($R^{12})_2]_n$C—CH, —[C($R^{12})_2]_n CON(R^{12})_2$, —[C($R^{12})_2]_n CONR^{12}N(R^{12})_2$, O—[C($R^{12})_2]_n CON(R^{12})_2$, O—[C($R^2)_2]_n CONR^2N(R^2)_2$, $NR^{12}$COA, $NR^{12}CON(R^{12})_2$, $NR^{12}SO_2A$, $N(SO_2A)_2$, $COR^{12}$, $S(O)_m$Ar, $SO_2NR^2$ or $NR^2$ or $S(O)_mA$,
$R^3$ and $R^4$ together also denote CH=CH—CH=CH,
$R^3$ and $R^4$, $R^7$ and $R^8$ or $R^8$ and $R^9$ together also denote alkylene having 3, 4 or 5 C atoms, in which one or two $CH_2$ groups may be replaced by oxygen, A denotes unbranched or branched alkyl having 1-6 C atoms, in which 1-7H atoms may be replaced by F, or cyclic alkyl having 3-7 C atoms, Ar denotes phenyl, naphthyl or biphenyl, each of which is unsubstituted or mono-, di- or trisubstituted by Hal, A, $OR^{12}$, $N(R^{12})_2$, $NO_2$, CN, phenyl, $CON(R^{12})_2$, $NR^{12}COA$, $NR^{12}CON(R^{12})_2$, $NR^{12}SO_2A$, $COR^{12}$, $SO_2N(R^{12})_2$, $S(O)_mA$, $-[C(R^{12})_2]_n-COOR^{12}$ and/or $-O[C(R^{12})_2]_n-COOR^{12}$, Het denotes a mono- or bicyclic saturated, unsaturated or aromatic heterocycle having 1 to 4 N, O and/or S atoms, which may be mono-, di- or trisubstituted by Hal, A, $OR^{12}$, $N(R^{12})_2$, $NO_2$, CN, $COOR^{12}CON(R^{12})_2$, $NR^{12}COA$, $NR^{12}SO_2A$, $COR^{12}$, $SO_2NR^{12}$, $S(O)_mA$, =S, $=NR^{12}$ and/or =O (carbonyl oxygen), $R^{12}$ denotes H or A, Hal denotes F, Cl, Br or I, m denotes 0, 1 or 2, n denotes 0, 1, 2 or 3, and o denotes 1, 2 or 3.

Small molecule SGK1 inhibitors have further been described in U.S. 2008/0167380 by Gericke et al. U.S. 2008/0167380 describes acyl hydrazides of the Formula (C), in which $R^1-R^9$ are defined in the specification as described below:

Formula (C)

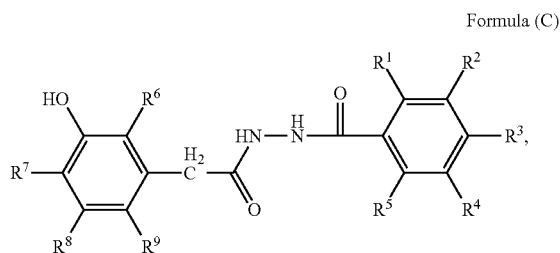

in which $R^1, R^2, R^3, R^4, R^5, R^6, R^7, R^8$, and $R^9$ each, independently of one another, denote H, A, $OSO_2A$, Hal, $NO_2$, $OR^{10}$, $N(R^{10})_2$, CN, $-[C(R^{10})_2]_nCOOR^{10}$, $O-[C(R^{10})_2]_o COOR^{10}$, $SO_3H$, $-[C(R^{10})_2]_nAr$, $-CO-Ar$, $O-[C(R^{10})_2]_nAr$, $-[C(R^{10})_2]_nHet$, $-[C(R^{10})_2]_nC\equiv CH$, $O-[C(R^{10})_2]_nC\equiv CH$, $-[C(R^{10})_2]_nCON(R^{10})_2$, $-[C(R^{10})_2]_nCONR^{10}N(R^{10})_2$, $O-[C(R^{10})_2]_nCON(R^{10})_2$, $O-[C(R^{10})_2]_oCONR^{10}N(R^{10})_2$, $NR^{10}COA$, $NR^{10}CON(R^{10})_2$, $NR^{10}SO_2A$, $N(SO_2A)_2$, $COR^{10}$, $S(O)_mAr$, $SO_2NR^{10}$ or $S(O)_mA$, or $R^1$ and $R^2$, $R^2$ and $R^3$, $R^3$ and $R^4$ or $R^4$ and $R^5$ together also denote CH=CH—CH=CH, A denotes unbranched or branched alkyl having 1-6 C atoms, in which 1-7H atoms may be replaced by F, or cyclic alkyl having 3-7 C atoms, Ar denotes phenyl, naphthyl or biphenyl, each of which is unsubstituted or mono-, di- or trisubstituted by Hal, A, $OR^{10}$, $N(R^{10})_2$, $NO_2$, CN, phenyl, $CON(R^{10})_2$, $NR^{10}COA$, $NR^{10}CON(R^{10})_2$, $NR^{10}SO_2A$, $COR^{10}$, $SO_2N(R^{10})_2$, $S(O)_mA$, $-[C(R^{10})_2]_n-COOR^{10}$ and/or $-O[C(R^{10})_2]_o-COOR^{10}$, Het denotes a mono- or bicyclic saturated, unsaturated or aromatic heterocycle having 1 to 4 N, O and/or S atoms, which may be mono-, di- or trisubstituted by Hal, A, $OR^{10}$, $N(R^{10})_2$, $NO_2$, CN, $COOR^{10}CON(R^{10})_2$, $NR^{10}COA$, $NR^{10}SO_2A$, $COR^{10}$, $SO_2NR^{10}$, $S(O)_mA$, =S, $=NR^{10}$ and/or =O (carbonyl oxygen), $R^{10}$ denotes H or A, Hal denotes F, Cl, Br or I, m denotes 0, 1 or 2, n denotes 0, 1, 2 or 3, and o denotes 1, 2 or 3.

Small molecule SGK1 inhibitors are also described in U.S. 2008/0234348 by Mederski et al. U.S. 2008/0234348 describes squaric acid compounds of the Formula (D) in which R1, R2, R2', R2" and X are defined in the specification as described below:

Formula (D)

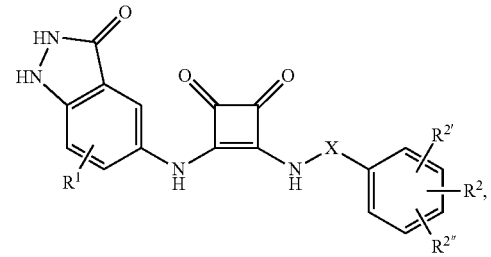

in which $R^1$ denotes H, A, Hal, CN, $NO_2$, C(=O)A, CHO, CH(OH)A, $NH_2$, NH(C=O)A, COOH, COOA, $SO_2NH_2$, $CONH_2$, $CONA_2$, $(CH_2)_mAr$ or Het, $R^2$ denotes OH, OA, Hal, $CF_3$, $SO_2NH_2$, NHAc or $NHSO_2A$, $R^{2'}$, $R^{2''}$ each, independently of one another, denote H or Hal, Ac denotes acetyl, Ar denotes phenyl which is unsubstituted or mono-, di- or trisubstituted by Hal, A, OH, OA, $NH_2$, $NO_2$, CN, COOH, COOA, $CONH_2$, NHCOA, $NHCONH_2$, $NHSO_2A$, $SO_2NH_2$ and/or $S(O)_mA$, Het denotes furyl, thienyl, pyrrolyl, imidazolyl, pyridyl, pyrimidinyl, pyrazolyl, thiazolyl or indolyl, each of which is unsubstituted or mono-, di- or trisubstituted by A, Hal, OH and/or OA, A denotes unbranched or branched alkyl having 1-10 C atoms, in which 1-7H atoms may be replaced by F, X is absent or denotes $CH_2$, CHA, $CA_2$ or

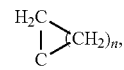

Hal denotes F, Cl, Br or I, m denotes 0, 1 or 2, and n denotes 1, 2, 3 or 4.

Small molecule SGK1 inhibitors are further described in U.S. 2009/0253767 by Klein et al. U.S. 2009/0253767 describes aminoindazolylurea derivatives of the Formula (E) in which $R^1$, $R^{2'}$ $R^3$, $R^4$, $R^5$, X and Y are defined in the specification as described below:

Formula (E)

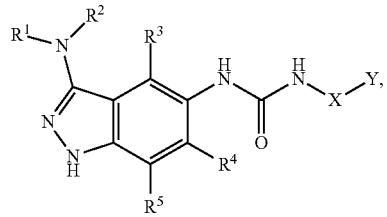

in which $R^1$, $R^2$ each, independently of one another, denote H, A, $-[C(R^7)_2]_nAr$, $-[C(R^7)_2]_nHet$, —COHet or —COAr, $R^3$, $R^4$, $R^5$ each, independently of one another, denote H, A, Hal, OH, OA, $-[C(R^7)_2]_nAr$, $-[C(R^7)_2]_nHet$, OAr, OHet, SH, SA, SAr, SHet, NH$_2$, NHA, NAA', NHAr, N(Ar)$_2$, NHHet, N(Het)$_2$, NAAr, NAHet, SOA, SOAr, SOHet, SO$_2$A, SO$_2$Ar, SO$_2$Het, NO$_2$, CN, COOH, COOA, CONH$_2$, CONHA, CONA$_2$, NHCOA, NACOA, NHCONH$_2$, NHCONHA, NHCONA$_2$, NHSO$_2$A, NASO$_2$A, CHO, COA, COAr, COHet, SO$_3$H, SO$_2$NH$_2$, SO$_2$NHAr, SO$_2$N(Ar)$_2$, SO$_2$NHHet or SO$_2$N(Het)$_2$, X denotes —CR$^7$R$^8$—, —CR$^7$R$^8$CR$^9$R$^1$— or —CR$^7$R$^8$C(OR$^9$)R$^{10}$—

Y denotes Ar or Het,

R$^7$, R$^8$, R$^9$, R$^{10}$ each, independently of one another, denote H or A, R$^{11}$ denotes alkyl having 1-6 C atoms, in which 1-5H atoms may be replaced by F, A, A' each, independently of one another, denote alkyl having 1-10 C atoms which is unsubstituted or mono-, di- or trisubstituted by R$^3$, =S, =NR$^7$ and/or =O (carbonyl oxygen) and in which one, two or three CH$_2$ groups may be replaced by O, S, SO, SO$_2$, NH, NR$^{11}$ and/or by —CH=CH— groups and/or, in addition, 1-7H atoms may be replaced by F and/or Cl, or cyclic alkyl having 3-7 C atoms, Ar denotes phenyl, naphthyl or biphenyl, each of which is unsubstituted or mono-, di-, tri- or tetrasubstituted by A, Hal, OH, OA, Ar', OAr', Het, OHet, SH, SA, SAr', SHet, NH$_2$, NHA, NAA', NHAr', N(Ar')$_2$, NHHet, N(Het)$_2$, NAAr', NAHet, SOA, SOAr', SOHet, SO$_2$A, SO$_2$Ar', SO$_2$Het, NO$_2$, CN, COOH, COOA, CONH$_2$, CONHA, CONA$_2$, NHCOA, NACOA, NHCONH$_2$, NHCONHA, NHCONA$_2$, NHSO$_2$A, NASO$_2$A, CHO, COA, COAr', COHet, SO$_3$H, SO$_2$NH$_2$, SO$_2$NHAr', SO$_2$N(Ar')$_2$, SO$_2$NHHet and/or SO$_2$N(Het)$_2$, Het denotes a mono- or bicyclic saturated, unsaturated or aromatic heterocycle having 1 to 4 N, O and/or S atoms, which may be mono-, di- or trisubstituted by A, Hal, OH, OA, Ar, OAr, Het', OHet', SH, SA, SAr', SHet', NH$_2$, NHA, NAA', NHAr, N(Ar')$_2$, NHHet', N(Het')$_2$, NAAr', NAHet', SOA, SOAr', SOHet', SO$_2$A, SO$_2$Ar', SO$_2$Het', NO$_2$, CN, COOH, COOA, CONH$_2$, CONHA, CONA$_2$, NHCOA, NACOA, NHCONH$_2$, NHCONHA, NHCONA$_2$, NHSO$_2$A, NASO$_2$A, CHO, COA, COAr', COHet', SO$_3$H, SO$_2$NH$_2$, SO$_2$NHAr', SO$_2$N(Ar')$_2$, SO$_2$NHHet' or SO$_2$N(Het')$_2$, =S, =NR$^7$ and/or =O (carbonyl oxygen), Ar' denotes phenyl which is unsubstituted or mono-, di-, tri- or tetrasubstituted by A, Hal, OH, OA, O-phenyl, SH, SA, NH$_2$, NHA, NAA', NH-phenyl, SOA, SO-phenyl, SO$_2$A, SO$_2$-phenyl, NO$_2$, CN, COOH, COOA, CONH$_2$, CONHA, CONA$_2$, NHCOA, NACOA, NHCONH$_2$, NHCONHA, NHCONA$_2$, NHSO$_2$A, NASO$_2$A, CHO, COA, CO— phenyl, SO$_3$H, SO$_2$NH$_2$, SO$_2$NH-phenyl and/or SO$_2$N(phenyl)$_2$, Het' denotes a mono- or bicyclic saturated, unsaturated or aromatic heterocycle having 1 to 4 N, O and/or S atoms, which may be mono-, di- or trisubstituted by A, Hal, OH, OA, NH$_2$, NHA, NAA', SOA, SOAr', SO$_2$A, SO$_2$Ar', NO$_2$, CN, COOH, COOA, CONH$_2$, CONHA, CONA$_2$, NHCOA, NACOA, NHCONH$_2$, NHCONHA, NHCONA$_2$, NHSO$_2$A, NASO$_2$A, CHO, COA, COAr', SO$_3$H, SO$_2$NH$_2$, SO$_2$NHAr', SO$_2$N(Ar')$_2$, =S, =NR$^7$ and/or =O (carbonyl oxygen), Hal denotes F, Cl, Br or I, and n denotes 0, 1 or 2.

Small molecule SGK1 inhibitors are also described in U.S. 2010/0063115 by Klein et al. U.S. 2010/0063115 describes aminoindazolylurea derivatives of the Formula (F) in which L, X, Y, R$^3$, R$^4$ and R$^5$ are described in the specification:

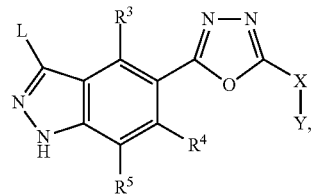

Formula (F)

in which

L denotes R$^1$, R$^2$ or —(X)$_m$R$^3$,

X denotes CR$^7$R$^8$, CR$^7$R$^8$CR$^9$R$^{10}$, CR$^7$R$^8$C(OR$^9$)R$^{10}$, NR$^7$, O, NR$^6$CR$^7$R$^8$, CR$^7$R$^8$NR$^9$, OCR$^7$R$^8$, OCR$^7$R$^8$CR$^9$R$^{10}$, CR$^7$R$^8$O, CR$^7$R$^8$CR$^9$R$^{10}$O, NR$^6$CR$^7$R$^8$CR$^9$R$^{10}$, CR$^7$R$^8$SO$_2$, NR$^7$CONR$^8$, NR$^7$CONR$^8$CR$^9$R$^{10}$, COCR$^7$R$^8$, CONR$^7$, CONR$^7$CR$^8$R$^9$, NR$^7$CR$^8$R$^9$CONR$^{10}$, NR$^7$CO or NR$^7$COCR$^8$R$^9$, Y denotes H, A, Ar or Het, R$^1$ denotes CR$^9$=CR$^9$R$^{10}$ or CR$^{12}$=CR$^{13}$R$^{14}$, R$^2$ denotes C≡CR$^{12}$ or C≡C-Het, R$^3$, R$^4$, R$^5$ each, independently of one another, denote H, A, Hal, OH, OA, —[C(R$^7$)$_2$]$_n$Ar, —[C(R$^7$)$_2$]$_n$Het, OAr, OHet, S H, SA, SAr, S Het, NH$_2$, NHA, NAA', NHAr, N(Ar)$_2$, NHHet, N(Het)$_2$, NAAr, NAHet, SOA, SOAr, SOHet, SO$_2$A, SO$_2$Ar, SO$_2$Het, NO$_2$, CN, COOH, COOA, CONH$_2$, CONHA, CONA$_2$, NHCOA, NACOA, NHCONH$_2$, NHCONHA, NHCONA$_2$, NHSO$_2$A, NASO$_2$A, CHO, COA, COAr, COHet, SO3H, SO$_2$NH$_2$, SO$_2$NHAr, SO$_2$N(Ar)$_2$, SO$_2$NHHet or SO$_2$N(Het)$_2$, R$^6$, R$^7$, R$^8$, R$^9$, R$^{10}$ each, independently of one another, denote H or A, R$^{11}$ denotes alkyl having 1-6 C atoms, in which 1-5 H atoms may be replaced by F, R$^{12}$, R$^{13}$, R$^{14}$ each, independently of one another, denote H or Ar, A, A' each, independently of one another, denote alkyl having 1-10 C atoms which is unsubstituted or mono-, di- or trisubstituted by R$^3$, =S, =NR$^7$ and/or =O (carbonyl oxygen) and in which one, two or three CH$_2$ groups may be replaced by O, S, SO, SO$_2$, NH, NR$^{11}$ and/or by —CH=CH-groups and/or, in addition, 1-7 H atoms may be replaced by F and/or Cl, or cyclic alkyl having 3-7 C atoms, Ar denotes phenyl, naphthyl or biphenyl, each of which is unsubstituted or mono-, di-, tri- or tetrasubstituted by A, Hal, OH, OA, Ar', OAr', Het, OHet, S H, SA, SAr', S Het, NH$_2$, NHA, NAA', NHAr', N(Ar')$_2$, NHHet, N(Het)$_2$, NAAr', NAHet, SOA, SOAr', SOHet, SO$_2$A, SO$_2$Ar', SO$_2$Het, NO$_2$, CN, COOH, COOA, CONH$_2$, CONHA, CONA$_2$, NHCOA, NACOA, NHCONH$_2$, NHCONHA, NHCONA$_2$, NHSO$_2$A, NASO$_2$A, CHO, COA, COAr', COHet, 5O$_3$H, SO$_2$NH$_2$, SO$_2$NHAr', SO$_2$N(Ar')$_2$, SO$_2$NHHet and/or SO$_2$N(Het)$_2$, Het denotes a mono- or bicyclic saturated, unsaturated or aromatic heterocycle having 1 to 4 N, O and/or S atoms, which may be mono-, di- or trisubstituted by A, Hal, OH, OA, Ar, OAr, Het', OHet', SH, SA, SAr', SHet', NH$_2$, NHA, NAA', NHAr, N(Ar')$_2$, NHHet', N(Het')$_2$, NAAr', NAHet', SOA, SOAr', SOHet', SO$_2$A, SO$_2$Ar', SO$_2$Het', NO$_2$, CN, COOH, COOA, CONH$_2$, CONHA, CONA$_2$, NHCOA, NACOA, NHCONH$_2$, NHCONHA, NHCONA$_2$, NHSO$_2$A, NASO$_2$A, CHO, COA, COAr', COHet', SO$_3$H, SO$_2$NH$_2$, SO$_2$NHAr', SO$_2$N(Ar')$_2$, SO$_2$NHHet' or SO$_2$N(Het')$_2$, =S, =NR$^7$ and/or =O (carbonyl oxygen), Ar' denotes phenyl which is unsubstituted or mono-, di-, tri- or tetrasubstituted by A, Hal, OH, OA, O-phenyl, SH, SA, NH₂, NHA, NAA', NH-phenyl, SOA, SO-phenyl, SO₂A, SO₂-phenyl, NO₂, CN, COOH, COOA, CONH₂, CONHA, CONA₂, NHCOA, NACOA, NHCONH₂, NHCONHA, NHCONA₂, NHSO₂A, NASO₂A, CHO, COA, CO-phenyl, SO₃H, SO₂NH₂, SO₂NH-phenyl and/or SO₂N(phenyl)₂, Het' denotes a mono- or bicyclic saturated, unsaturated or aromatic heterocycle having 1 to 4 N, O and/or S atoms, which may be mono-, di- or trisubstituted by A, Hal, OH, OA, NH₂, NHA, NAA', SOA, SOAr', SO₂A, SO₂Ar', NO₂, CN, COOH, COOA, CONH₂, CONHA, CONA₂, NHCOA, NACOA, NHCONH₂, NHCONHA, NHCONA₂, NHSO₂A, NASO₂A, CHO, COA, COAr', SO₃H, SO₂NH₂, SO₂NHAr', SO₂N(Ar')₂, =S, =NR⁷ and/or =O (carbonyl oxygen), Hal denotes F, Cl, Br or I, m denotes 0, 1, 2 or 3, and n denotes 0, 1 or 2.

Small molecule SGK1 inhibitors are yet further described in WO 2008/021725 by Drewry et al. WO 2008/021725 describes pyridine isoquinoline derivatives of the Formula (G) in which X, Y, and R are defined in the specification:

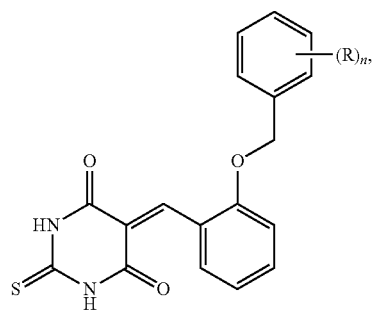

Formula (G)

in which

X is O or S.

Y is O or S.

R is selected from:

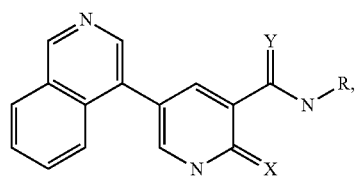

(CH₂)ₙR¹, wherein n is 1, 2, or 3 and R¹ is aryl;

heteroaryl optionally substituted with one or more groups independently selected from the group consisting of C₁-C₃ alkyl and oxo; and aryl optionally substituted with one or more groups independently selected from the group consisting of d₋₃ alkyl, d₋₃ alkoxy, halo, C$_{r3}$ haloalkyl, d₋₃ hydroxyalkyl, —C(O)NH₂, —OH, —CN, C$_{r3}$ haloalkoxy, aryloxy, —(CH₂)$_p$S(O)₂NH₂, and —(CH₂)$_q$NRᵃRᵇ; wherein:

p is 0, 1, 2, 3, 4, 5, or 6;

q is 1, 2, 3, 4, 5, or 6;

Rᵃ is H or C₁₋₃ alkyl; and

Rᵇ is H or C₁₋₃ alkyl.

Additional small molecule inhibitors of SGK1 can include compounds of the Formula 1:

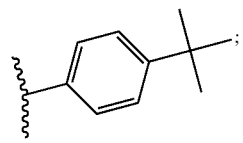 [SMILES: *c1ccc(C(C)(C)C)cc1]

(Formula 1)

wherein n is 1, 2, 3, 4, or 5; each R is independently selected from the group consisting of hydrogen, a halogen, C₁-C₆ alkyl, C₁-C₆ alkoxy, C₁-C₆ haloalkyl, C₁-C₆ haloalkoxy, CN, CO₂H, CO₂(C₁-C₆ alkyl), CO₂(C₁-C₆ haloalkyl), —OH, —NH₂, —NH(C₁-C₆ alkyl), —N(C₁-C₆ alkyl)₂, —SH, and —S(C₁-C₆ alkyl); or a pharmaceutically acceptable salt thereof.

Exemplary small molecule inhibitors of SGK1 include:

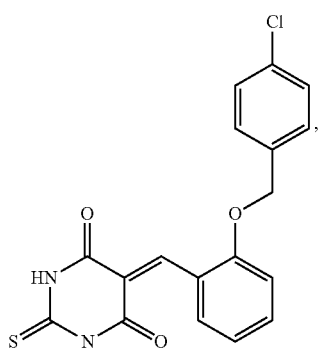

(1A)

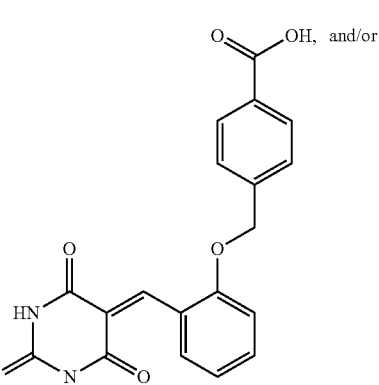

(1B)

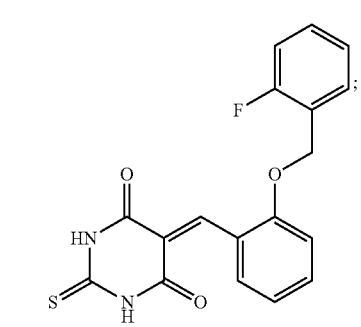

(1C)

or a pharmaceutically acceptable salt thereof.

These three compounds were purchased from ChemBridge (San Diego, Calif.) (catalogue numbers 5377051 for 1A, 6333540 for 1B, and 6347949 for 1C).

Additional examples of SGK1 inhibitors can include antibodies or antigen-binding fragments thereof that selectively bind an SGK1 protein. The term "antibody" is intended to encompass all types of polyclonal and monoclonal antibodies (e.g., human, chimeric, humanized, primatized, veneered, single chain, domain antibodies (dAbs)) and antigen-binding fragments of antibodies (e.g., Fv, Fc, Fd, Fab, Fab', F(ab'), dAb). (See e.g., Harlow et al., *Antibodies A Laboratory Manual*, Cold Spring Harbor Laboratory, 1988). In a particular embodiment, an SGK1-specific antibody is a human antibody or humanized antibody. SGK1-specific antibodies can also be directly or indirectly linked to a cytotoxic agent.

Several antibodies that selectively bind SGK1 have been produced and are commercially available (e.g. from Abcam®, Cell Signaling Technology®, EMD Millipore, Sigma-Aldrich®, and Santa Cruz Biotechnology, Inc.).

Other antibodies or antibody fragments which can serve as SGK1 inhibitors can also be produced, constructed, engineered, and/or isolated by conventional methods or other suitable techniques. For example, antibodies which are specific for an SGK1 protein (and thus serve as SGK1 inhibitors) can be raised against an appropriate immunogen, such as a recombinant mammalian (e.g., human) SGK1 protein or portion thereof (including synthetic molecules, e.g., synthetic peptides). A variety of methods have been described (see e.g., Kohler et al., *Nature*, 256: 495-497 (1975) and *Eur. J. Immunol.* 6: 511-519 (1976); Milstein et al., *Nature* 266: 550-552 (1977); Koprowski et al., U.S. Pat. No. 4,172,124; Harlow, E. and D. Lane, 1988, *Antibodies: A Laboratory Manual*, (Cold Spring Harbor Laboratory: Cold Spring Harbor, N.Y.); *Current Protocols In Molecular Biology*, Vol. 2 (Supplement 27, Summer '94), Ausubel, F. M. et al., Eds., (John Wiley & Sons: New York, N.Y.), Chapter 11, (1991)).

Antibodies can also be raised by immunizing a suitable host (e.g., mouse) with cells that express SGK1 (e.g., cardiovascular cells/cell lines) or cells engineered to express SGK1 (e.g., transfected cells). (See e.g., Chuntharapai et al., *J. Immunol.*, 152:1783-1789 (1994); Chuntharapai et al. U.S. Pat. No. 5,440,021). For the production of monoclonal antibodies, a hybridoma can be produced by fusing a suitable immortal cell line (e.g., a myeloma cell line such as SP2/0 or P3X63Ag8.653) with antibody producing cells. The antibody-producing cells can be obtained from the peripheral blood, or preferably, the spleen or lymph nodes, of humans or other suitable animals immunized with the antigen of interest. The fused cells (hybridomas) can be isolated using selective culture conditions, and cloned by limited dilution. Cells which produce antibodies with the desired specificity can be selected by a suitable assay (e.g., ELISA).

Antibody fragments can be produced by enzymatic cleavage or by recombinant techniques. For example, papain or pepsin cleavage can generate Fab or F(ab')$_2$ fragments, respectively. Other proteases with the requisite substrate specificity can also be used to generate Fab or F(ab')$_2$ fragments. Antibodies can also be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the CH$_1$ domain and hinge region of the heavy chain. Single chain antibodies, and human, chimeric, humanized or primatized (CDR-grafted), or veneered antibodies, as well as chimeric, CDR-grafted or veneered single chain antibodies, comprising portions derived from different species, and the like are also encompassed by the present invention and the term "antibody". The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0 451 216 B1; and Padlan, E. A. et al., EP 0 519 596 A1. See also, Newman, R. et al., *BioTechnology*, 10: 1455-1460 (1992), regarding primatized antibody, and Ladner et al., U.S. Pat. No. 4,946,778 and Bird, R. E. et al., *Science*, 242: 423-426 (1988)) regarding single chain antibodies.

Humanized antibodies can be produced using synthetic or recombinant DNA technology using standard methods or other suitable techniques. Nucleic acid (e.g., cDNA) sequences coding for humanized variable regions can also be constructed using PCR mutagenesis methods to alter DNA sequences encoding a human or humanized chain, such as a DNA template from a previously humanized variable region (see e.g., Kamman, M., et al., *Nucl. Acids Res.*, 17: 5404 (1989)); Sato, K., et al., *Cancer Research*, 53: 851-856 (1993); Daugherty, B. L. et al., *Nucleic Acids Res.*, 19(9): 2471-2476 (1991); and Lewis, A. P. and J. S. Crowe, *Gene*, 101: 297-302 (1991)). Using these or other suitable methods, variants can also be readily produced. In one embodiment, cloned variable regions (e.g., dAbs) can be mutated, and sequences encoding variants with the desired specificity can be selected (e.g., from a phage library; see e.g., Krebber et al. U.S. Pat. No. 5,514,548; Hoogenboom et al., WO 93/06213, published Apr. 1, 1993).

Other suitable methods of producing or isolating antibodies of the requisite specificity can be used, including, for example, methods which select a recombinant antibody or antibody-binding fragment (e.g., dAbs) from a library (e.g., a phage display library), or which rely upon immunization of transgenic animals (e.g., mice). Transgenic animals capable of producing a repertoire of human antibodies are well-known in the art (e.g., Xenomouse® (Abgenix, Fremont, Calif.)) and can be produced using suitable methods (see e.g., Jakobovits et al., *Proc. Natl. Acad. Sci. USA*, 90: 2551-2555 (1993); Jakobovits et al., *Nature*, 362: 255-258 (1993); Lonberg et al., U.S. Pat. No. 5,545,806; Surani et al., U.S. Pat. No. 5,545,807; Lonberg et al., WO 97/13852).

SGK1 inhibitors are also agents that inhibit (reduce, decrease, prevent, block, arrest or interfere with) the expression of an SGK1 protein. In one or more embodiments, the SGK1 inhibitor is a miRNA, a siRNA, a shRNA, a dsRNA or an antisense RNA directed to SGK1 DNA or mRNA; a polynucleotide encoding the miRNA, siRNA, shRNA, dsRNA or antisense RNA; or an equivalent of each thereof.

Agents (small molecules, peptides, nucleic acids, oligonucleotides) that inhibit SGK1 gene expression (e.g., transcription, mRNA processing, translation) can be effective SGK1 inhibitors. For example, small interfering ribonucleic acids (siRNAs) and, similarly, short hairpin ribonucleic acids (shRNAs) which are processed into short siRNA-like molecules in a cell, can prevent the expression (translation)

of the SGK1 protein. siRNA molecules can be polynucleotides that are generally about 20 to about 25 nucleotides long and are designed to bind specific RNA sequence (e.g., SGK1 mRNA). siRNAs silence gene expression in a sequence-specific manner, binding to a target RNA (e.g., an RNA having the complementary sequence) and causing the RNA to be degraded by endoribonucleases. siRNA molecules able to inhibit the expression of the SGK1 gene product can be produced by suitable methods. There are several algorithms that can be used to design siRNA molecules that bind the sequence of a gene of interest (see e.g., Mateeva O. et al. *Nucleic Acids Res.* 35(8):Epub, 2007; Huesken D. et al., *Nat. Biotechnol.* 23:995-1001; Jagla B. et al., *RNA* 11:864-872, 2005; Shabalinea S. A. *BMC Bioinformatics* 7:65, 2005; Vert J. P. et al. *BMC Bioinformatics* 7:520, 2006). Expression vectors that can stably express siRNA or shRNA are available. (See e.g., Brummelkamp, T. R., *Science* 296: 550-553, 2002, Lee, N S, et al., *Nature Biotechnol.* 20:500-505, 2002; Miyagishi, M., and Taira, K. *Nature Biotechnol.* 20:497-500, 2002; Paddison, P. J., et al., *Genes & Dev.* 16:948-958, 2002; Paul, C. P., et al., *Nature Biotechnol.* 20:505-508; 2002; Sui, G., et al., *Proc. Natl. Acad. Sci. USA* 99(6):5515-5520, 2002; Yu, J-Y, et al., *Proc. Natl. Acad. Sci. USA* 99(9):6047-6052, 2002; Elbashir, S M, et al., *Nature* 411:494-498, 2001.).

"Short interfering RNAs" (siRNA) refer to double-stranded RNA molecules (dsRNA), generally, from about 10 to about 30 nucleotides in length that are capable of mediating RNA interference (RNAi). "RNA interference" (RNAi) refers to sequence-specific or gene specific suppression of gene expression (protein synthesis) that is mediated by short interfering RNA (siRNA). As used herein, the term siRNA includes short hairpin RNAs (shRNAs). A siRNA directed to a gene or the mRNA of a gene may be a siRNA that recognizes the mRNA of the gene and directs a RNA-induced silencing complex (RISC) to the mRNA, leading to degradation of the mRNA. A siRNA directed to a gene or the mRNA of a gene may also be a siRNA that recognizes the mRNA and inhibits translation of the mRNA. A siRNA may be chemically modified to increase its stability and safety. See, e.g. Dykxhoorn and Lieberman (2006) Annu. Rev. Biomed. Eng. 8:377-402 and U.S. Patent Application Publication No.: 2008/0249055.

"Double stranded RNAs" (dsRNA) refer to double stranded RNA molecules that may be of any length and may be cleaved intracellularly into smaller RNA molecules, such as siRNA. In cells that have a competent interferon response, longer dsRNA, such as those longer than about 30 base pair in length, may trigger the interferon response. In other cells that do not have a competent interferon response, dsRNA may be used to trigger specific RNAi.

"MicroRNAs" (miRNA) refer to single-stranded RNA molecules of 21-23 nucleotides in length, which regulate gene expression. miRNAs are encoded by genes from whose DNA they are transcribed but miRNAs are not translated into protein (non-coding RNA); instead each primary transcript (a pri-miRNA) is processed into a short stem-loop structure called a pre-miRNA and finally into a functional miRNA. Mature miRNA molecules are partially complementary to one or more messenger RNA (mRNA) molecules, and their main function is to down-regulate gene expression.

siRNA, dsRNA, and miRNA to inhibit SGK1 gene expression can be designed following procedures known in the art. See, e.g., Dykxhoorn and Lieberman (2006) Annu. Rev. Biomed. Eng. 8:377-402; Dykxhoorn et al. (2006) Gene Therapy 13:541-52; Aagaard and Rossi (2007) Adv. Drug Delivery Rev. 59:75-86; de Fougerolles et al. (2007) Nature Reviews Drug Discovery 6:443-53; Krueger et al. (2007) Oligonucleotides 17:237-250; U.S. Patent Application Publication No.: 2008/0188430; and U.S. Patent Application Publication No.: 2008/0249055.

Delivery of siRNA, dsRNA or miRNA to a cell can be made with methods known in the art. See, e.g., Dykxhoorn and Lieberman (2006) Annu. Rev. Biomed. Eng. 8:377-402; Dykxhoorn et al. (2006) Gene Therapy 13:541-52; Aagaard and Rossi (2007) Adv. Drug Delivery Rev. 59:75-86; de Fougerolles et al. (2007) Nature Reviews Drug Discovery 6:443-53; Krueger et al. (2007) Oligonucleotides 17:237-250; U.S. Patent Application Publication No.: 2008/0188430; and U.S. Patent Application Publication No.: 2008/0249055.

Antisense oligonucleotides (e.g., RNA, DNA, riboprobes) can also be used as SGK1 inhibitors to inhibit SGK1 expression. Antisense oligonucleotides are generally short (~13 to ~25 nucleotides) single-stranded nucleic acids which specifically hybridize to a target nucleic acid sequence (e.g., mRNA or DNA) and induce the degradation of the target nucleic acid (e.g., degradation of the RNA through RNase H-dependent mechanisms) or sterically hinder the progression of splicing or translational machinery. (See e.g., Dias N. and Stein C. A., *Mol. Can. Ther.* 1:347-355, 2002). There are a number of different types of antisense oligonucleotides that can be used as SGK1 inhibitors including methylphosphonate oligonucleotides, phosphorothioate oligonucleotides, oligonucleotides having a hydrogen at the 2'-position of ribose replaced by an O-alkyl group (e.g., a methyl), polyamide nucleic acid (PNA), phosphorodiamidate morpholino oligomers (deoxyribose moiety is replaced by a morpholine ring), PN (N3'→P5' replacement of the oxygen at the 3' position on ribose by an amine group) and chimeric oligonucleotides (e.g., 2'-O-Methyl/phosphorothioate). Antisense oligonucleotides can be designed to be specific for an SGK1 protein using predictive algorithms. (See e.g., Ding, Y., and Lawrence, C. E., *Nucleic Acids Res.*, 29:1034-1046, 2001; Sczakiel, G., *Front. Biosci.*, 5:D194-D201, 2000; Scherr, M., et al., *Nucleic Acids Res.*, 28:2455-2461, 2000; Patzel, V., et al. *Nucleic Acids Res.*, 27:4328-4334, 1999; Chiang, M. Y., et al., *J. Biol. Chem.*, 266:18162-18171, 1991; Stull, R. A., et al., *Nucleic Acids Res.*, 20:3501-3508, 1992; Ding, Y., and Lawrence, C. E., *Comput. Chem.*, 23:387-400, 1999; Lloyd, B. H., et al., *Nucleic Acids Res.*, 29:3664-3673, 2001; Mir, K. U., and Southern, E. M., *Nat. Biotechnol.*, 17:788-792, 1999; Sohail, M., et al., *Nucleic Acids Res.*, 29:2041-2051, 2001; Altman, R. K., et al., *J. Comb. Chem.*, 1:493-508, 1999). The antisense oligonucleotides can be produced by suitable methods; for example, nucleic acid (e.g., DNA, RNA, PNA) synthesis using an automated nucleic acid synthesizer (from, e.g., Applied Biosystems) (see also Martin, P., *Helv. Chim. Acta* 78:486-504, 1995). Antisense oligonucleotides can also be stably expressed in a cell containing an appropriate expression vector.

Antisense oligonucleotides can be taken up by target cells (e.g., cardiac cells) via the process of adsorptive endocytosis. Thus, in the treatment of a subject (e.g., mammalian), antisense SGK1 oligonucleotides can be delivered to target cells (e.g., cardiac myocytes and/or other cardiac cells) by, for example, injection or infusion. For instance, purified oligonucleotides or siRNA/shRNA, can be administered alone or in a formulation with a suitable drug delivery vehicle (e.g., liposomes, cationic polymers, (e.g., poly-L-lysine.PAMAM dendrimers, polyalkylcyanoacrylate nanoparticles and polyethyleneimine) or coupled to a suitable carrier peptide (e.g., homeotic transcription factor, the Antennapedia peptide, Tat protein of HIV-1, ESCA peptide).

It will be appreciated that the oligonucleotides can be made using nonstandard bases (e.g., other than adenine, cytidine, guanine, thymine, and uridine) or nonstandard backbone structures to provide desirable properties (e.g., increased nuclease-resistance, tighter-binding, stability or a desired $T_m$). Techniques for rendering oligonucleotides nuclease-resistant include those described in PCT Publication WO 94/12633. A wide variety of useful modified oligonucleotides may be produced, including oligonucleotides having a peptide-nucleic acid (PNA) backbone (Nielsen et al. (1991) Science 254:1497) or incorporating 2'-O-methyl ribonucleotides, phosphorothioate nucleotides, methyl phosphonate nucleotides, phosphotriester nucleotides, phosphorothioate nucleotides, phosphoramidates. Another example of the modification is replacement of a non-bridging phosphoryl oxygen atom with a sulfur atom which increases resistance to nuclease digestion. Increased antisense polynucleotide stability can also be achieved using molecules with 2-methyoxyethyl substituted backbones. See e.g., U.S. Pat. Nos. 6,451,991 and 6,900,187.

Ribozymes can also be used as SGK1 inhibitors to inhibit SGK1 expression. Ribozymes are RNA molecules possessing enzymatic activity. One class of ribozymes is capable of repeatedly cleaving other separate RNA molecules into two or more pieces in a nucleotide base sequence specific manner. See Kim et al., *Proc Natl Acad Sci USA*, 84:8788 (1987); Haseloff & Gerlach, *Nature*, 334:585 (1988); and Jefferies et al., *Nucleic Acid Res*, 17:1371 (1989). Such ribozymes typically have two functional domains: a catalytic domain and a binding sequence that guides the binding of ribozymes to a target RNA through complementary base-pairing. Once a specifically-designed ribozyme is bound to a target mRNA, it enzymatically cleaves the target mRNA, typically reducing its stability and destroying its ability to directly translate an encoded protein. After a ribozyme has cleaved its RNA target, it is released from that target RNA and thereafter can bind and cleave another target. That is, a single ribozyme molecule can repeatedly bind and cleave new targets.

In accordance with the present invention, a ribozyme may target any portion of the mRNA encoding SGK1. Methods for selecting a ribozyme target sequence and designing and making ribozymes are generally known in the art. See e.g., U.S. Pat. Nos. 4,987,071; 5,496,698; 5,525,468; 5,631,359; 5,646,020; 5,672,511; and 6,140,491, each of which is incorporated herein by reference in its entirety. For example, suitable ribozymes may be designed in various configurations such as hammerhead motifs, hairpin motifs, hepatitis delta virus motifs, group I intron motifs, or RNase P RNA motifs. See e.g., U.S. Pat. Nos. 4,987,071; 5,496,698; 5,525, 468; 5,631,359; 5,646,020; 5,672,511; and 6,140,491; Rossi et al., *AIDS Res Human Retroviruses* 8:183 (1992); Hampel & Tritz, *Biochemistry* 28:4929 (1989); Hampel et al., *Nucleic Acids Res*, 18:299 (1990); Perrotta & Been, *Biochemistry* 31:16 (1992); and Guerrier-Takada et al., *Cell*, 35:849 (1983).

Ribozymes can be synthesized by the same methods used for normal RNA synthesis. For example, suitable methods are disclosed in Usman et al., *J Am Chem Soc*, 109:7845-7854 (1987) and Scaringe et al., *Nucleic Acids Res*, 18:5433-5441 (1990). Modified ribozymes may be synthesized by the methods disclosed in, e.g., U.S. Pat. No. 5,652,094; International Publication Nos. WO 91/03162; WO 92/07065 and WO 93/15187; European Patent Application No. 92110298.4; Perrault et al., *Nature*, 344:565 (1990); Pieken et al., *Science*, 253:314 (1991); and Usman & Cedergren, *Trends Biochem Sci*, 17:334 (1992).

"Triplex ribozymes" configurations allow for increased target cleavage relative to conventionally expressed ribozymes. Examples of triplex ribozymes include hairpin ribozymes and hammerhead ribozymes. Methods of making and using triplex ribozymes are found in, e.g., Aguino-Jarguin et al. (2008) Oligonucleotides 18(3):213-24 and U.S. Patent Application Publication No. 2005/0260163.

Proteins have been described that have the ability to translocate desired nucleic acids across a cell membrane. Typically, such proteins have amphiphilic or hydrophobic subsequences that have the ability to act as membrane-translocating carriers. For example, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz (1996) Current Opinion in Neurobiology 6:629-634. Another subsequence, the h (hydrophobic) domain of signal peptides, was found to have similar cell membrane translocation characteristics (see, e.g., Lin et al. (1995) J. Biol. Chem. 270:14255-14258). Such subsequences can be used to translocate oligonucleotides across a cell membrane. Oligonucleotides can be conveniently derivatized with such sequences. For example, a linker can be used to link the oligonucleotides and the translocation sequence. Any suitable linker can be used, e.g., a peptide linker or any other suitable chemical linker.

The present invention provides, in one embodiment, a polypeptide decoy that mimics a domain necessary for the action of SGK1. A polypeptide decoy of a protein for inhibiting the interaction between the protein and a substrate is a polypeptide that binds to the substrate but does not carry out the biological activity that such a binding would normally carry out. In one embodiment, a polypeptide decoy is a fragment of the SGK1 protein. For instance, a polypeptide decoy can comprise a 5 to 10, 10 to 15, 15 to 20, 20-25, 25-30, 30-40, 40-45 or more than 45 amino acid fragment thereof that regulates the myo-inositol transporter during osmotic stress. A polypeptide decoy can also arise from other modifications of an SGK1 protein, for instance through glycosylation or phosphorylation, or by designing similar systems that mimic peptides, such as using peptoids, D-amino acids or β-peptides. A peptide decoy that mimics the SGK1 protein can also arise from an alteration of the backbone of SGK1. SGK1 inhibitors can also include a cDNA or mRNA that encodes a portion or the full coding sequence of SGK1 that has been mutated in a way that will interfere with or inhibit the activity of the endogenous SGK1, a construct commonly called a "dominant negative".

The SGK1 inhibitors described herein for a therapeutic use may be administered with an acceptable pharmaceutical carrier. Acceptable "pharmaceutical carriers" are well known to those of skill in the art and can include, but not be limited to any of the standard pharmaceutical carriers, such as phosphate buffered saline, water and emulsions, such as oil/water emulsions and various types of wetting agents. Suitable pharmaceutical carriers can contain inert ingredients which do not interact with the SGK1 inhibitor. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's lactate and the like. Formulations can also include small amounts of substances that enhance the effectiveness of the active ingredient (e.g., emulsifying, solubilizing, pH buffering, wetting agents). Methods of encapsulation compositions (such as in a coating of hard gelatin or cyclodextran) are known in the art. For inhalation, the agent can be solubilized and loaded into a suitable dispenser for administration (e.g., an atomizer or nebulizer or pressurized aerosol dispenser).

Agents having SGK1 binding specificity, including small molecules, or any other SGK1 inhibitor described herein can be identified in a screen, for example, a high-throughput screen of chemical compounds and/or libraries (e.g., chemical, peptide, nucleic acid libraries). Compounds or small molecules can be identified from numerous available libraries of chemical compounds from, for example, the Chemical Repository of the National Cancer Institute and the Molecular Libraries Small Molecules Repository (PubChem), as well as libraries of the Institute of Chemistry and Cell Biology at Harvard University and other libraries that are available from commercial sources (e.g., Chembridge, Peakdale, CEREP, MayBridge, Bionet). Such libraries or collections of molecules can also be prepared using well-known chemical methods, such as well-known methods of combinatorial chemistry. The libraries can be screened to identify compounds that bind and inhibit SGK1. Identified compounds can serve as lead compounds for further diversification using well-known methods of medicinal chemistry. For example, a collection of compounds that are structural variants of the lead can be prepared and screened for SGK1 binding and/or inhibitory activity. This can result in the development of a structure activity relationship that links the structure of the compounds to biological activity. Compounds that have suitable binding and inhibitory activity can be developed further for in vivo use. Suitable assays for SGK1 are described in, for instance, Example 3, US 2008/0234348 (Mederski et al.), WO 2008/021725 (Drewry et al.), and WO 2005/106491 (Golz et al.).

The term "treatment" is meant administering a pharmaceutical composition for the purpose of therapeutic treatment by reducing, alleviating or reversing at least one adverse effect or symptom.

The term "administering" means providing the subject with an effective amount of the SGK1 inhibitor effective to treat a disease or condition in the subject. Methods of administering pharmaceutical compositions are well known to those of skill in the art and include, but are not limited to, microinjection, intravenous or parenteral administration. The compositions are intended for systemic, topical, oral, or local administration as well as intravenously, subcutaneously, or intramuscularly. Administration can be effected continuously or intermittently throughout the course of treatment. Methods of determining the most effective means and dosage of administration are well known to those of skill in the art and will vary with the vector used for therapy, the polypeptide or protein used for therapy, the purpose of the therapy, the target cell being treated, and the subject being treated. Single or multiple administrations can be carried out with the dose level and pattern being selected by the treating physician. For example, the compositions can be administered prior to a subject already suffering from a disease or condition that is linked to apoptosis.

The term "therapeutically effective amount" refers to a quantity of compound (e.g., an SGK1 inhibitor) delivered with sufficient frequency to provide a medical benefit to the patient. In one embodiment, an effective amount of an SGK1 inhibitor is an amount sufficient to treat or ameliorate a symptom of Long QT syndrome or an immune complex mediated disease. Exemplary effective amounts of an SGK1 inhibitor range from 0.1 ug/kg body weight to 100 mg/kg body weight; alternatively 1.0 ug/kg body weight to 10 mg/kg body weight.

A "subject" includes mammals, e.g., humans, companion animals (e.g., dogs, cats, birds and the like), farm animals (e.g., cows, sheep, pigs, horses, fowl and the like) and laboratory animals (e.g., rats, mice, guinea pigs and the like). In a preferred embodiment of the disclosed methods, the subject is human.

Another embodiment of the invention is a pharmaceutical composition comprising the compound of Formula 1, 1A, 1B or 1C, or a pharmaceutically acceptable salt thereof, and a pharmaceutically acceptable carrier or diluent. In one or more embodiments, the invention is a method of treatment of a disease including administration of a compound of Formula 1 (or a pharmaceutically acceptable salt thereof) or a pharmaceutical composition comprising a compound of Formula 1 (or a pharmaceutically acceptable salt thereof). In one or more embodiments, the invention is a method of treatment of a disease including administration of a pharmaceutical composition comprising a compound of Formula 1A, 1B, or 1C (or a pharmaceutically acceptable salt thereof). In one or more embodiments, the disease is diabetes (for example diabetes mellitus, diabetic nephropathy, diabetic neuropathy, diabetic angiopathy and microangiopathy), obesity, metabolic syndrome (dyslipidaemia), systemic and pulmonary hypertonia, cardiovascular diseases (for example cardiac fibroses after myocardial infarction, cardiac hypertrophy and cardiac insufficiency, arteriosclerosis) and renal diseases (for example glomerulosclerosis, nephrosclerosis, nephritis, nephropathy, electrolyte excretion disorder), fibroses and inflammatory processes of any type (for example liver cirrhosis, pulmonary fibrosis, fibrosing pancreatitis, rheumatism and arthroses, Crohn's disease, chronic bronchitis, radiation fibrosis, sclerodermatitis, cystic fibrosis, scarring, Alzheimer's disease), tumor cells and tumor metastases, coagulopathies, (such as, for example, dysfibrinogenaemia, hypoproconvertinaemia, haemophilia B, Stuart-Prower defect, prothrombin complex deficiency, consumption coagulopathy, hyperfibrinolysis, immunocoagulopathy or complex coagulopathies), neuronal excitability, (for example epilepsy), glaucoma, tinnitus or cataracts. A therapeutically effective amount of the compound (or a pharmaceutically acceptable salt thereof) is administered to the subject for the treatment of any of the foregoing diseases or condition In one or more embodiments, the compounds of Formula 1, 1A, 1B, or 1C (or a pharmaceutically acceptable salt thereof) can be furthermore used in the treatment of bacterial infections and in antiinfection therapy. The compounds can also be employed therapeutically for increasing learning ability and attention. In addition, the compounds can be used to counter cell ageing and stress and thus increase life expectancy and fitness in the elderly. A therapeutically effective amount of the compound (or a pharmaceutically acceptable salt thereof) is administered to the subject for the treatment of any of the foregoing diseases or condition.

The present invention is further defined in the following Examples. It should be understood that these Examples, while indicating preferred embodiments of the invention, are given by way of illustration only. The teachings of any publications described herein are hereby incorporated by reference in their entirety.

EXAMPLES

Example 1

SGK1 Activity Regulates Nav1.5-Mediated Sodium Flux

HEK 293 cells with a stably transfected SCN5a gene (referred to as HEK-Nav1.5) were transiently transfected with a plasmid expressing either a constitutively-active form of SGK1 (SGK1 S422D, referred to as SGK1-CA), a dominant negative form of SGK1 (SGK1 K127M, referred to as SGK1-DN) or the vector with an empty cassette. 48 hours after transfection, cells were studied by whole cell voltage clamping.

Figure 7A:
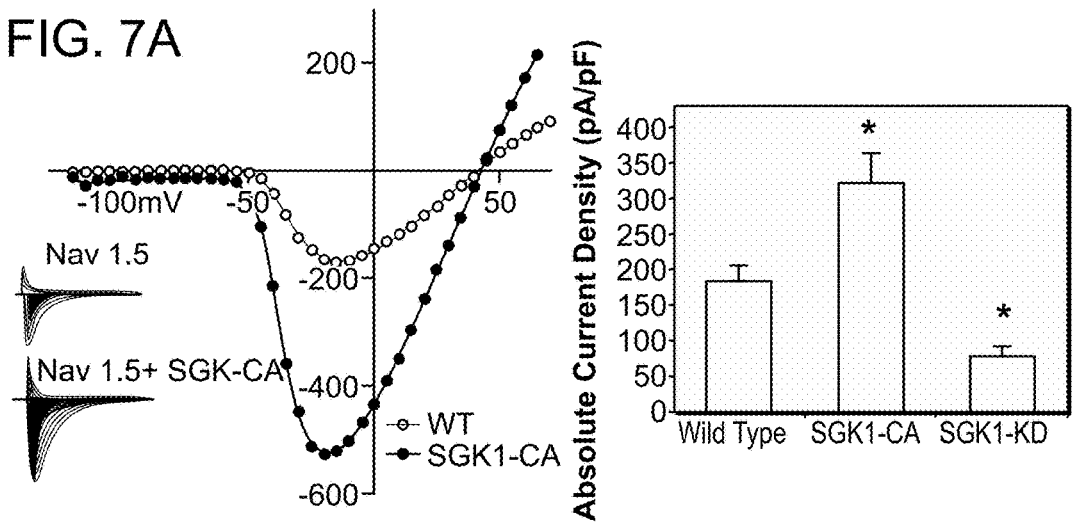
FIG. 7A-C show graphs regarding SGK1 regulates Nav 1.5 channel function.

Expression of SGK1-CA led to an increase, while expression of SGK1-DN led to a decrease in $I_{NA}$ current density (FIG. 7A), compared to empty plasmid. The fact that inhibition of SGK1 in cells transfected with SGK1-DN led to a decrease in $I_{NA}$ current density suggested that there is a baseline SGK1 activity that drive sodium flux in the cell.

Figure 7B:
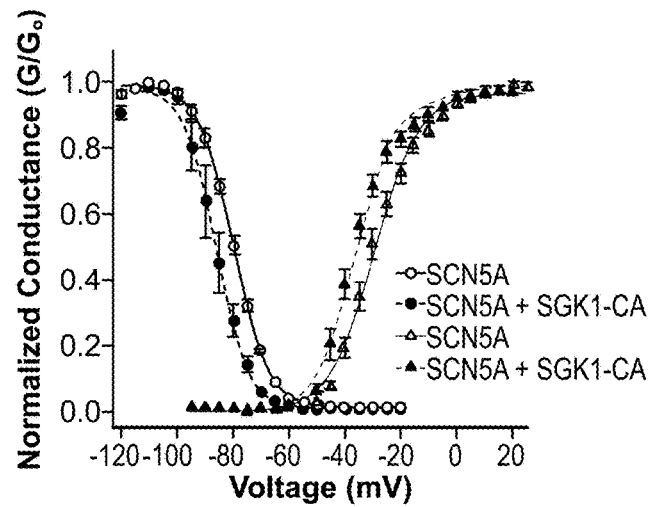

In addition, HEK-Nav1.5 cells transfected with SGK1-CA had left-ward (hyperpolarizing) shifts of their steady state activation and inactivation curves (FIG. 7B). This is also expected to increase the 'window' current, leading to an increase in $I_{NA}$.

Figure 7C:
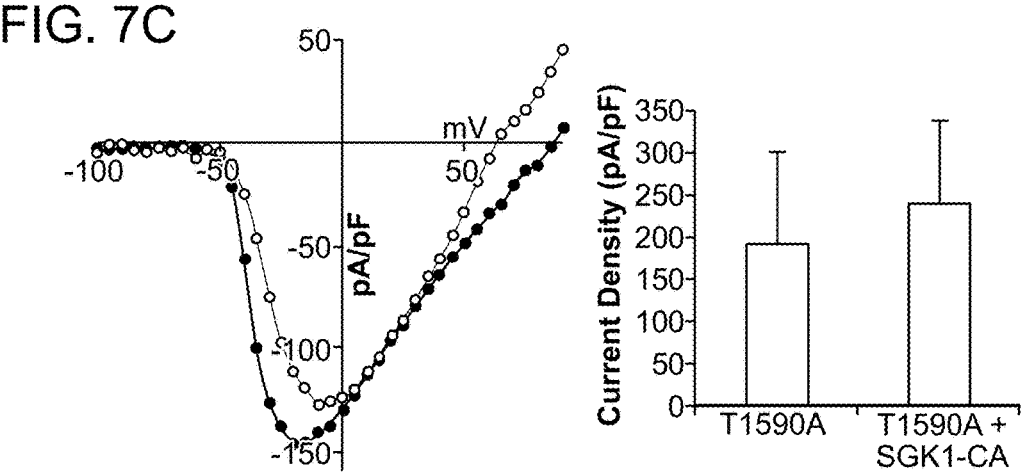

Three consensus sites for phosphorylation on Nav1.5 had been identified, including two sites in the linker between subdomains I and II, and a previously undescribed site on the C-terminal domain. The first two sites had been shown to influence channel biophysical properties in oocyte expression experiments. Mutation of the serines to alanines (to abolish SGK1 phosphorylation) also abolished the hyperpolarization shifts in the activation and inactivation curves described above. Mutation of the C-terminal residue (T1590A) to a non-phosphorylatable residue prevented the effects of SGK1 activation on $I_{NA}$ current density (FIG. 7C). Taken together, the data suggests that SGK1 regulates $I_{NA}$ in multiple different ways, and inhibition of SGK1 may be a novel manner to reduce $I_{NA}$ in pathological conditions.

Example 2

Genetic Inhibition of SGK1 Rescues 2:1 Phenotype in Bkd Mutant Zebrafish

The zebrafish breakdance mutant (Bkd-/-) fish is a unique model of action potential prolongation due to a mutation in the Zerg (zebrafish HERG) channel, that recapitulates human LQT2 syndrome and has been used in high throughput screens to identify molecules that may shorten the action potential duration. The phenotypic manifestation of the prolonged QT interval in the Bkd -/- fish is the presence of functional 2:1 AV block, and previous screens have taken advantage of this easily quantifiable phenotype to screen for 'rescue' from 2:1 AV block.

Bkd$^{-/-}$ (Breakdance) adults were crossed, and the resultant embryos were reared in E3 buffer at 25° C. 24 hours post-fertilization (hpf) animals were dechorionated with pronase and plated per well in 96-well plates in a final volume of 200 µL. At 48 hpf, compounds were added to the appropriate concentration. Zebrafish were visually scored at 72 hpf for presence or absence of 2:1 AV block. For the dose response curve, the fish at 48 hpf were treated for 24 hours at the desired concentration (from 20 mM stock in DMSO) and scored for suppression of breakdance phenotype. Genetic inhibition of SGK1 was achieved either by injection of 500 µM of SGK1 morpholino or SGK1-dominant negative mRNA at the 1-2 cell stage and the fish were scored for rescue of 2:1 AV block at the 99 hpf stage.

Bkd$^{-/-}$ fish injected with 500 µM of SGK1 morpholino or SGK1-DN mRNA (that have previously been shown to inhibit SGK1 activity in a dominant negative fashion) demonstrated significant rescue of the 2:1 AV block. SGK-1 morpholino showed rescue of 58% of mutants (compared with 5% spontaneous reversion in control scrambled morpholino injections). SGK1-DN was an even more potent in rescuing the phenotype (90% rescue) (FIG. 1). These results demonstrated that SGK1 inhibition could rescue the 2:1 AV block phenotype in this zebrafish model of LQTS. This may be due to shortening of the action potential duration and myocardial repolarization by modulation of ion channel function

Example 3

Compound 1A is Effective in Reversing the 2:1 Block in bkd Mutants

Figure 2:
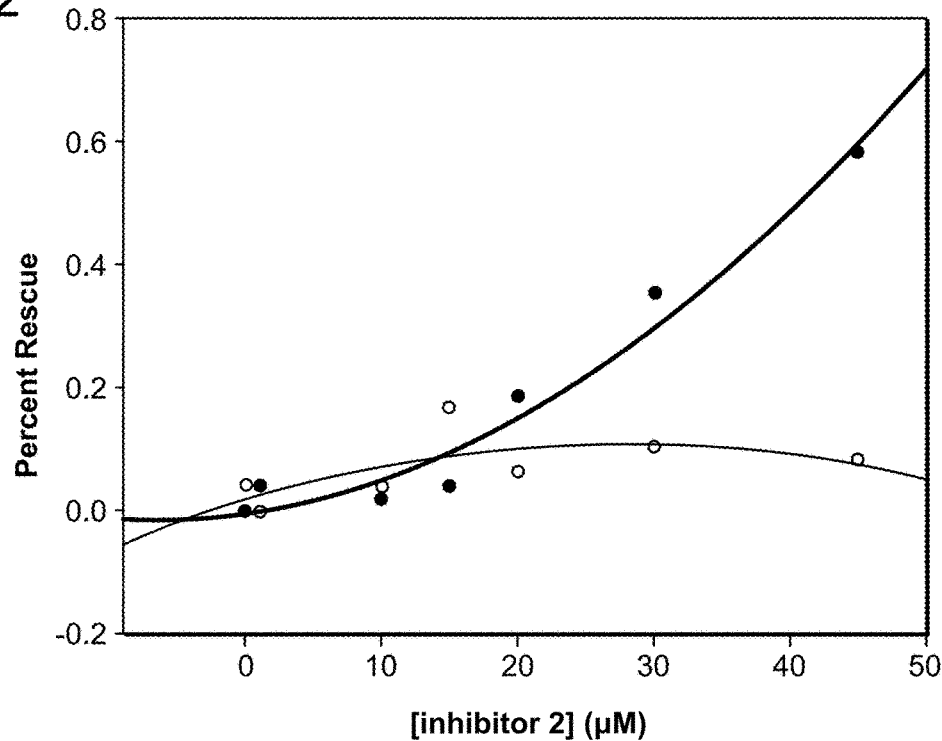
FIG. 2 shows that SGK1 inhibitor 2 (also identified as Compound 1A or Compound 5377051) rescues 2:1 AV block phenotype of the bkd$^{-/-}$ mutant zebrafish in a dose dependent manner Peak rescue occurs at 45 mM with no significant increase in toxicity seen in the dosages tested (gray line, open circles, right). Percent rescue at this concentration is comparable to rescue by morpholino.
Figure 2:
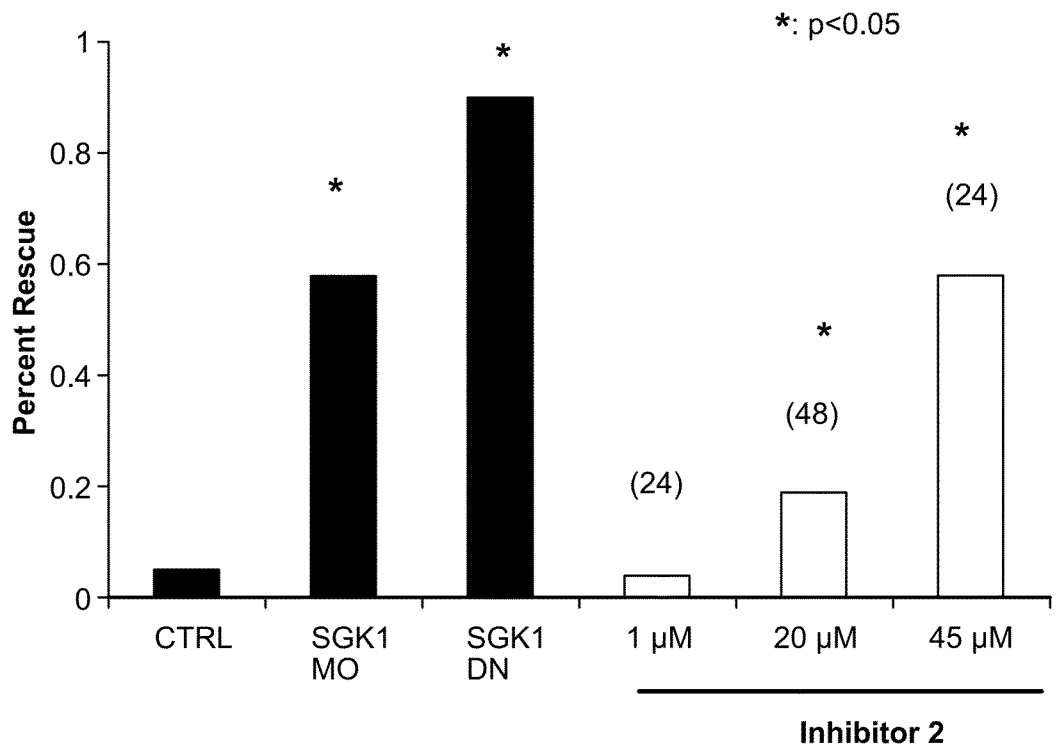

Bkd$^{-/-}$ fish treated with compound 1A at the concentrations indicated in FIG. 2 was effective at rescuing the 2:1 AV block phenotype with 58% rescue noted at a concentration of 45 µM with minimal and stable toxicity in concentrations up to 50 µM.

For Examples 4 and 5, to test the benefits of SGK1 inhibition, a kinase-dead, dominant negative mutant form of SGK1 was genetically expressed in the hearts of mice, under control of the myosin-heavy-chain-alpha promoter. These mice were normal at baseline, and subsequently subjected to either transvers aortic constriction (TAC)-induced pressure overload or transient surgical ligation of a coronary artery, to induce a heart attack.

Example 4

SGK1 Inhibition Mitigates the Effect of Pressure Overload

For TAC, 12 week old male mice were anesthetized and underwent thoracotomy at which time the transverse was constricted to the diameter of a blunted 25 G needle. Mice recovered and cardiac function was followed by echocardiography. Seven weeks after surgery, mice were euthanized for tissue studies including analysis of fibrosis.

Figure 4A:
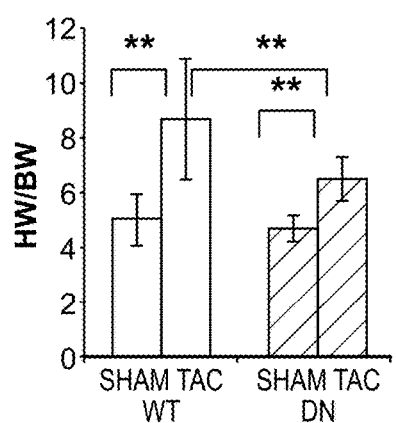
FIG. 4A shows a graph of the heart weight to body weight (HW/BW) ratios in SGK1-inhibited and wild-type mice following TAC.
Figure 4B:
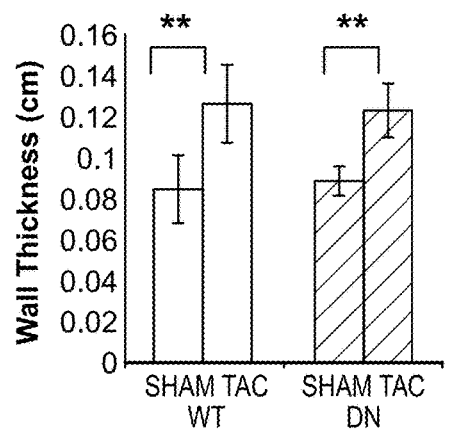
FIG. 4B shows a graph of left ventricle (LV) wall thickness in SGK1-inhibited and wild-type mice following TAC.
Figure 4C:
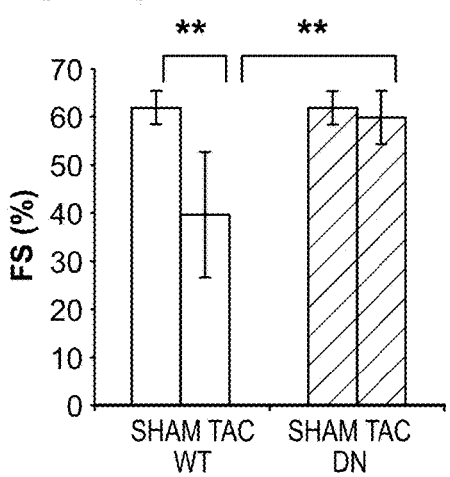
FIG. 4C shows a graph of fractional shortening (FS) in SGK1-inhibited and wild-type mice following TAC.
Figure 4D:
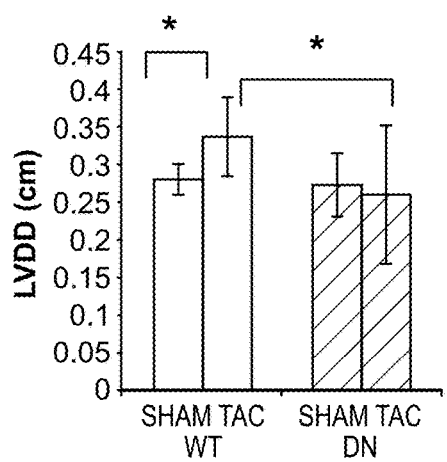
FIG. 4D shows a graph of LV dilation (LVDD) in SGK1-inhibited and wild-type mice following TAC.
Figure 4E:
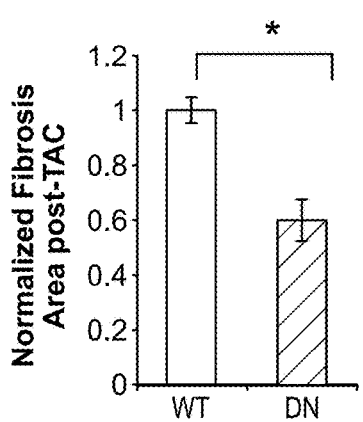
FIG. 4E shows a graph of normalized fibrosis area in SGK1-inhibited and wild-type mice following TAC.
Figure 4F:
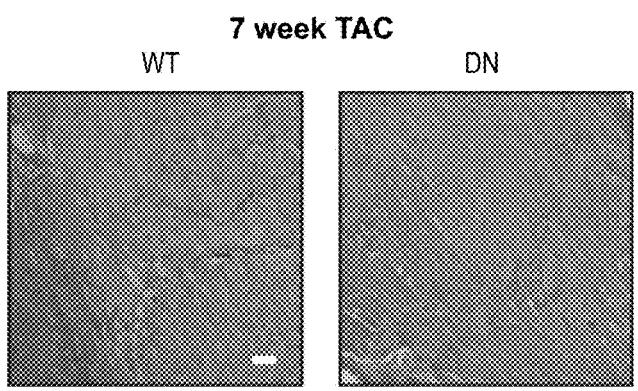
FIG. 4F shows histology of cardiac cells in SGK1-inhibited and wild-type mice following TAC.

Seven weeks after TAC, heart weight to body weight (HW/BW) ratios and left ventricular (LV) wall thickness increased less in SGK1-inhibited (SGK1-DN) than in wild-type (WT) littermates (FIG. 4A and FIG. 4B). Echocardiography seven weeks after TAC revealed reduced cardiac function (fractional shortening, FS) and increased LV dilatation (LVDD) in WT but not SGK1-DN mice (FIG. 4C and FIG. 4D). SGK1-DN mice also had significantly less fibrosis than WT mice after TAC (FIG. 4E). Thus, SGK1 inhibition protects against the development of heart failure, cardiac dilation, and fibrosis following pressure overload, which simulates events that occur in humans in response to hypertension or valvular stenosis.

Example 5

SGK1 Inhibition Reduces Injury and Improves Function After Ischemic Injury (Heart Attack)

Figure 5:
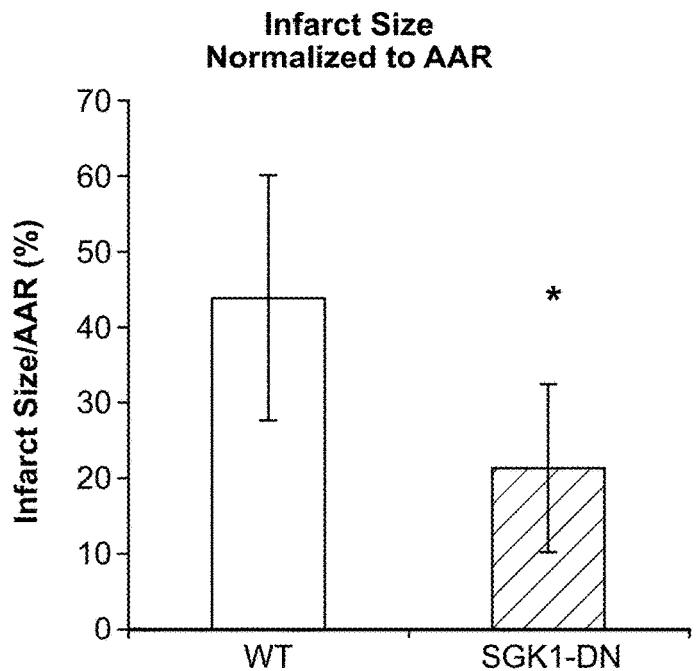
FIG. 5 shows a graph of infarct size (normalized to AAR) in SGK1-inhibited and wild-type mice following ischemic injury.

For ischemia-reperfusion injury (IRI) that simulates a heart attack receiving reperfusion therapy, the current standard of care, 12-week old SGK1-inhibited (SGK1-DN) mice and WT controls were subjected to 30 minutes of ischemia (with reversible left coronary ligation) followed by 24 hours of reperfusion. At twenty-four hours after IRI, hearts were analyzed for infarct size and "area-at-risk" (AAR) was assessed by injection of fluorescent microspheres at the time of infarction and area of infarct was assessed by TTC staining. Quantitation showed that there was a significant reduction (40%, p<0.04) in infarct size with chronic SGK1 inhibition compared with WT mice (FIG. 5). This reduction in infarct size (in response to the same ischemic stimulus) was associated with improved cardiac function as measured by echocardiography (FS, p<0.05) for at least two weeks after IRI.

Example 6

SGK1 is Activated in Human Dilated Cardiomyopathy (DCM)

Ventricular tissue from patients with hypertensive heart disease who died from non-cardiac causes (HHD) as well as explants from patients with heart failure and dilated cardiomyopathy (DCM) at the time of orthotopic transplantation was examined Healthy unused donor hearts served as controls. The cohorts were age and gender matched. Coronary angiograms had confirmed lack of significant epicardial coronary artery disease in the patients with DCM, and gravimetry confirmed a trend towards increased LV mass in patients with HHD (CTRL 363±133 gm, HHD 518±112 gm, p=0.07). In HHD hearts, there was an increase in total SGK1 (1.22±0.12, p<0.04) without a change in pSGK1 compared with controls. DCM hearts had a 2.3-fold increase in pSGK1 (2.3±0.85-fold, p<0.005 vs controls) without alterations in total SGK1. This phosphorylation site is indicative of SGK1 activation and correlates well with kinase activity. Thus these studies demonstrate that SGK1 is activated in human DCM.

Example 7

SGK1 Inhibition Mitigates Genetic DCM

Figure 6:
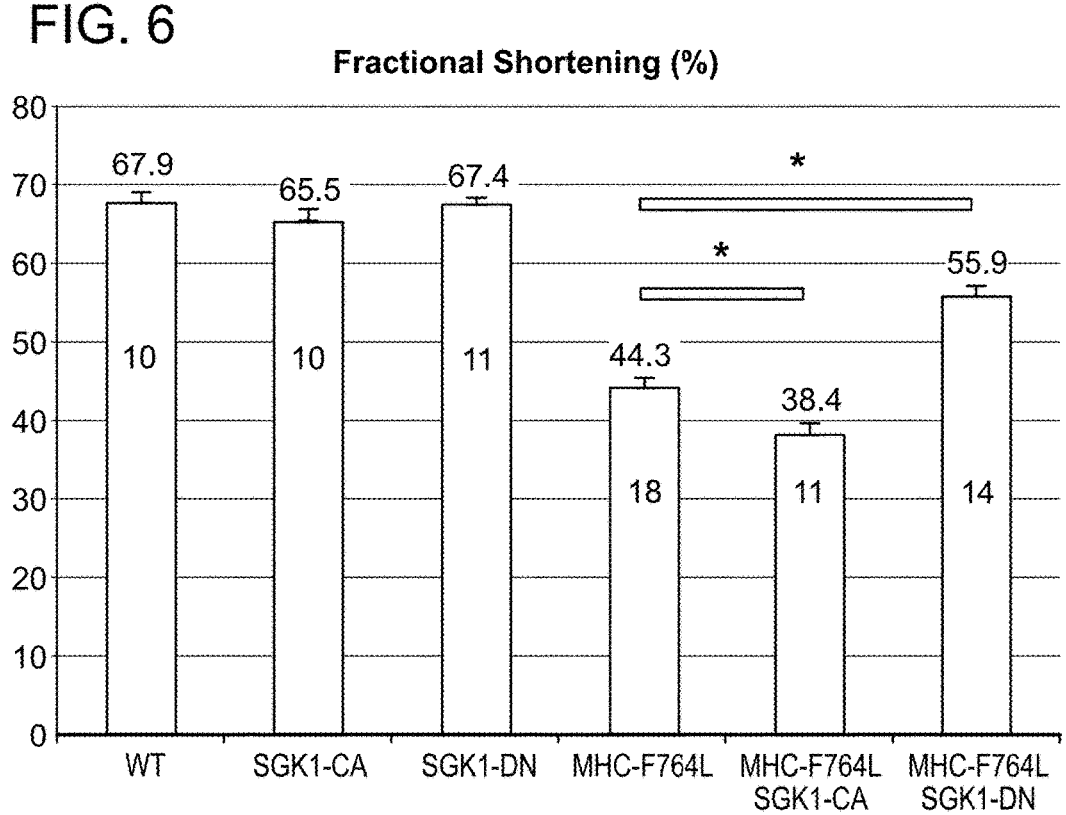
FIG. 6 shows a graph demonstrating that SGK1 inhibition improves cardiac function in MHC-F764L mice ($*p<0.05$).

To determine whether activation of SGK1 is functionally important in DCM, a well-characterized model of genetic DCM caused by a mutation in the myosin heavy chain (MHC-F764L) was selected. While this model is the result of a specific mutation, the gene involved is commonly mutated in cardiomyopathy and is a member of the class of structural proteins (involved in cytoskeleton and sarcomere function) that is most commonly mutated in DCM. SGK1 was activated or inhibited in MHC-F764L mice by breeding two mice expressing either a constitutively active (SGK1-CA) or dominant negative (SGK1-DN) SGK1 mutant. MHC-F764L heterozygotes (hets) have significant LV dysfunction compared to WT (FIG. 6, p<0.05). At 12 weeks, SGK1 activation (SGK1-CA) worsened fractional shortening (FS) in MHC-F764L hets, while SGK1 inhibition (SGK1-DN) substantially improved FS (FIG. 6, p<0.05).

Example 8

Discovery of Small Molecule SGK1 Inhibitors

Using a computational drug discovery platform, three iterative rounds of testing predicted inhibitors were performed in a polarization-based in-solution kinase assay using purified recombinant SGK1 protein and the inhibitors to identify three inhibitor 'lead compounds' that perform well in solution. Briefly, this assay utilizes a phosphorylated peptide that is labeled with a green fluorescent dye: this has a low molecular weight, hence a minimal fluorescence polarization value. This tracer binds to a phospho-specific antibody forming a high molecular weight complex with a high polarization value. In the kinase reaction, a competitive non-labeled peptide gets phosphorylated by the kinase and competes with the labeled tracer for binding with the antibody. With increased kinase activity, less labeled tracer is bound to the antibody, which in turn results in a decrease in fluorescence polarization. First, the reproducibility and dynamic range of the assay was validated using different concentrations of a recombinant GST-purified SGK-1 and determined the EC70 of the recombinant kinase to be 1 ng. This assay was then used in a high-throughput validation format to evaluate the $1^{st}$ and $2^{nd}$ generation small molecule inhibitors identified using our CADD platform. Initial activity screening was done at a concentration of 50☐M to ensure finding all compounds with activity and several compounds had demonstrable SGK1 inhibitory potential.

Figure 3:
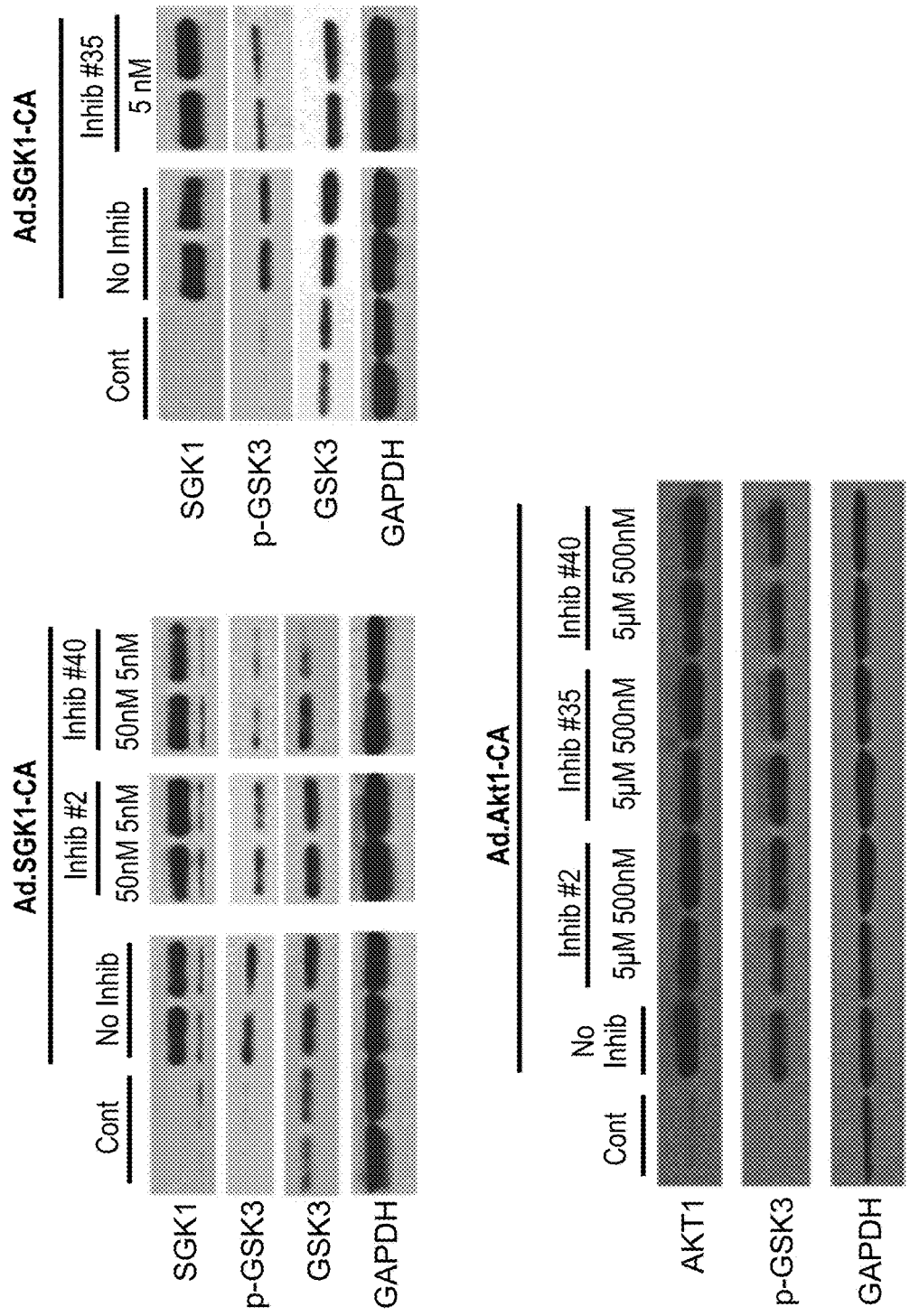
FIG. 3 shows cell-based assays for SGK1 inhibition.
Figure 8A:
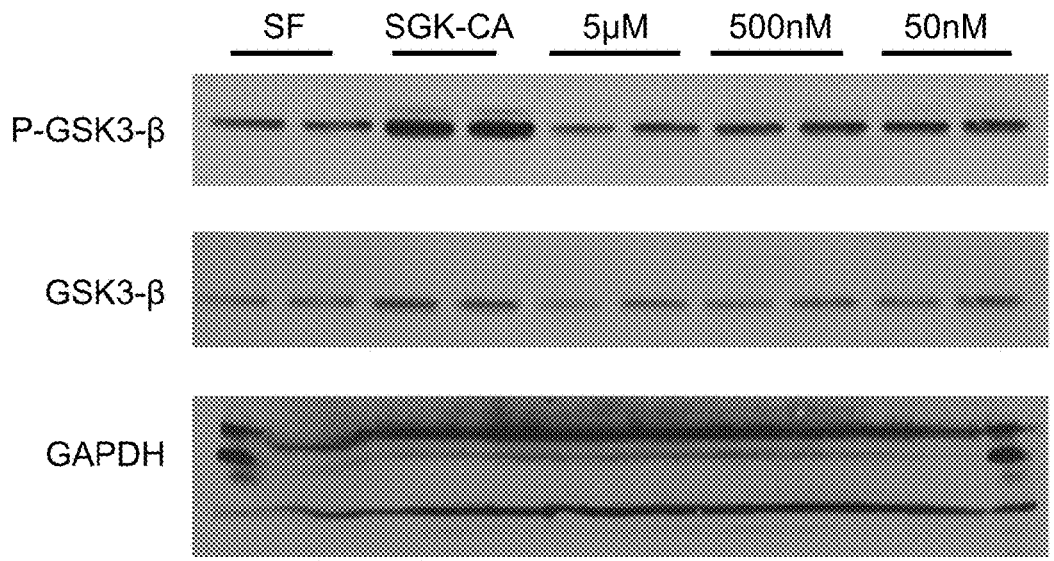
Figure 8A:
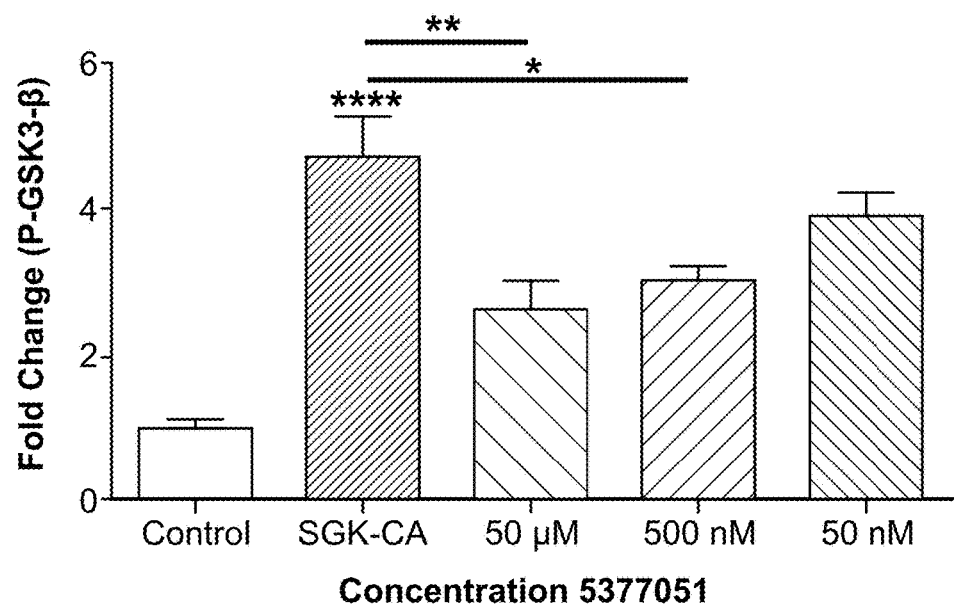
Figure 9:
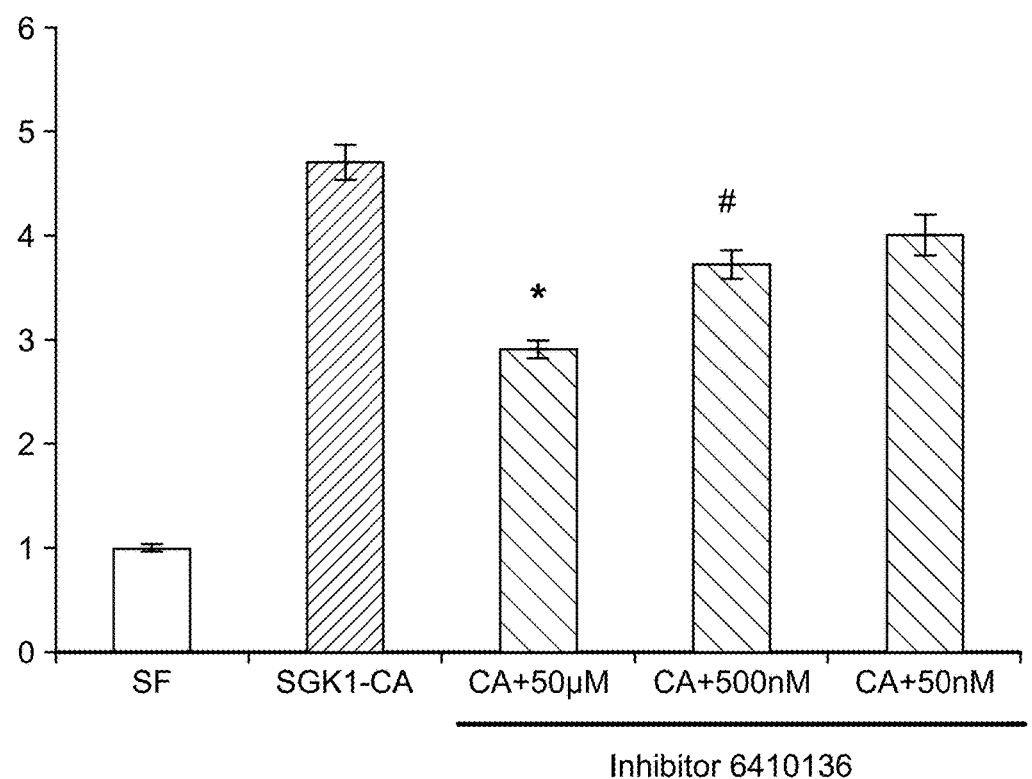
FIG. 9 shows inhibition of SGK1 activity in CMs transfected by Ad.SGK1-CA by inhibitor 6410136.

These inhibitors were further characterized using a cell-based cardiomyocyte system (FIG. 3). $2 \times 10^6$ neonatal rat ventricular myocytes (NRVMs) were plated on 60 mm plates in DMEM containing 10% horse serum, 5% fetal bovine serum, 1% L-glutamine and 1% penstrep antibiotic. 24 h after plating media was changed to DMEM containing 1% L-glutamine, and 24 h following cells were infected with SGK-CA virus and treated with various concentrations of SGK inhibitors 5377051 (Compound 1A) and 6410136 (Chembridge compound catalogue #6410136). 12 h after infection and treatment, the media was changed and cells were treated again. 12 h following the second treatment NRVMs were harvested and lysed in 300 uL of cell lysis buffer (Cell Signaling) containing protease and phosphatase inhibitors and PMSF at 4 degrees C. for 1 h with shaking. Lysates were subjected to immunoblotting with an antibody against phospho (ser38)-glycogen synthase kinase beta (p-GSK3β), a well-established SGK1 substrate. For gel electrophoresis, 50 ug of protein per well was loaded, transferred to nitrocellulose membrane, blocked, and incubated with GAPDH and P-GSK3β primary antibodies. As expected, Ad. SGK1-CA caused an increase in p-GSK3β, which was inhibited by both 5377051 and 6410136, suggesting inhibition of SGK1 in CMs (FIG. 8A, FIG. 9). The SGK1 inhibitors reproducibly and effectively reduced SGK1-driven phosphorylation of GSK-3β at concentrations in the 10-100's nM range (FIG. 3). In contrast, none of the inhibitors had a significant effect on Akt-mediated phosphorylation of GSK-3β even at significantly higher concentrations in a similar cardiomyocyte-based assay (FIG. 3).

Because SGK1 and Akt are structurally related but have very different roles in the heart, with Akt deemed to be cardioprotective against stress, the inhibitors were assessed to determine if they have an off-target effect on Akt in CMs. NRVMs were infected with adenoviral-driven constitutively active Akt (myr-Akt) or control adenovirus, and treated with the inhibitors as above. The levels of p-GSK3β, a common substrate for Akt and SGK1, were assesd again. While infection of NRVMs with Ad.myr-Akt caused an expected increase in p-GSK3β, neither 5377051 nor 6410136 caused a significant inhibition of this activity (FIG. 8B).

Figure 8C:
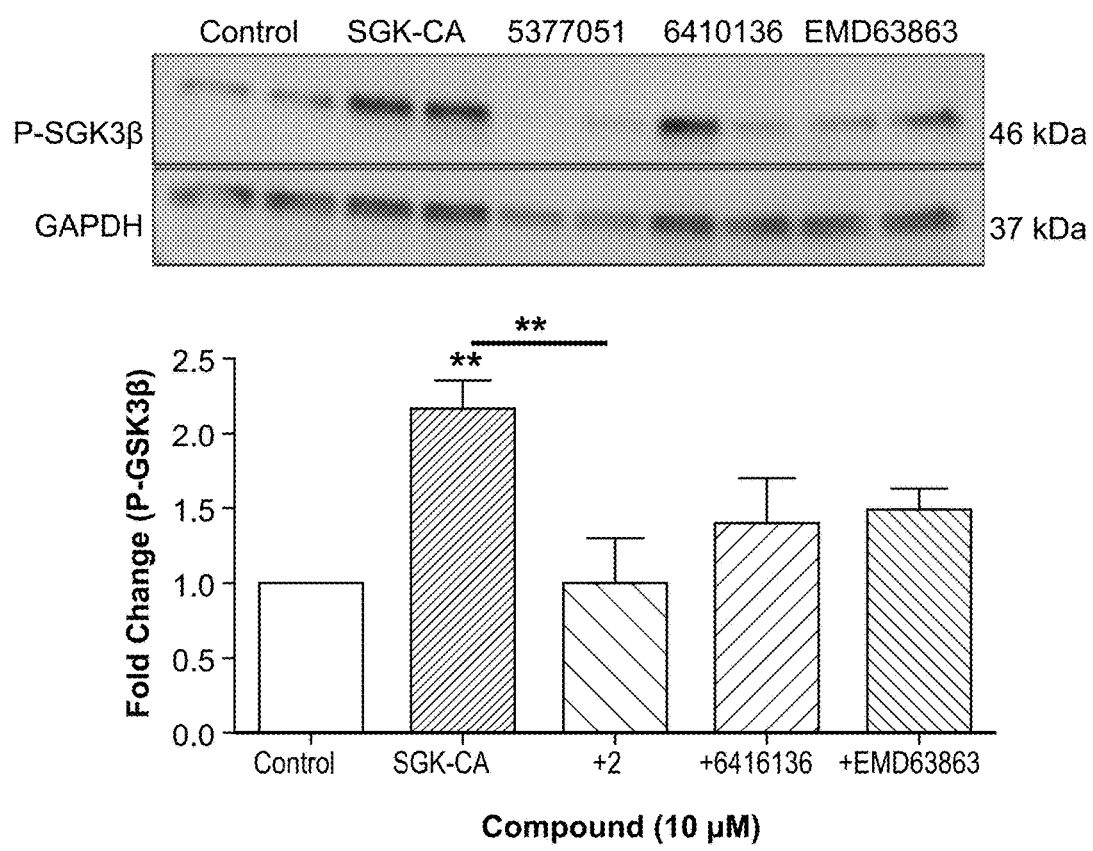

The activity of 5377051 and 6410136 were compared with a previously reported SGK1 inhibitor EMD 638683 in this cellular assay and found that the lead compounds of the instant invention were better or at least equivalent in their ability to inhibit SGK1 (FIG. 8C).

We claim:
1. A method for treatment of a cardiovascular disease in a subject, the method comprising, administering to the subject a therapeutically effective amount of at least one SGK1 inhibitor having the Formula 1:

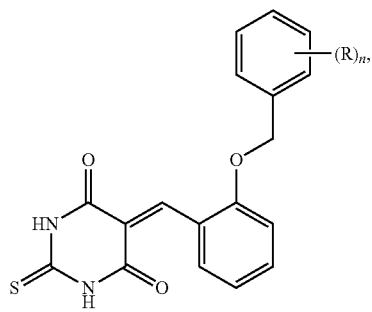

(Formula 1)

wherein:

n is 1, 2, 3, 4, or 5;

each R is independently selected from the group consisting of hydrogen, a halogen, $C_1$-$C_6$ alkyl, $C_1$-$C_6$ alkoxy, $C_1$-$C_6$ haloalkyl, $C_1$-$C_6$ haloalkoxy, CN, $CO_2H$, $CO_2$($C_1$-$C_6$ alkyl), $CO_2$($C_1$-$C_6$ haloalkyl), —OH, —$NH_2$, —NH($C_1$-$C_6$ alkyl), —N($C_1$-$C_6$ alkyl)$_2$, —SH, and —S($C_1$-$C_6$ alkyl);

or a pharmaceutically acceptable salt thereof, wherein the cardiovascular disease is selected from the group consisting of heart failure, arrhythmia, ischemic injury, ischemic infarction, cardiac fibrosis, vascular proliferation, restenosis, dilated cardiomyopathy, and stent failure.

2. The method of claim 1, wherein the cardiovascular disease is any one of the group selected from heart failure, arrhythmia, ischemic injury, ischemic infarction, cardiac fibrosis, vascular proliferation, restenosis, or stent failure.

3. The method of claim 1, wherein the cardiovascular disease is dilated cardiomyopathy.

4. The method of claim 3, wherein the dilated cardiomyopathy is genetic.

5. The method of claim 3, wherein the dilated cardiomyopathy is acquired.

6. The method of claim 4, wherein the dilated cardiomyopathy is characterized by a mutation in the MYH6 gene.

7. The method of claim 4, wherein the dilated cardiomyopathy is characterized by a mutation in the MYH7 gene.

8. The method of claim 4, wherein the dilated cardiomyopathy is characterized by a mutation in the SCN5A gene.

9. The method of claim 1, wherein the SGK1 inhibitor is selected from:

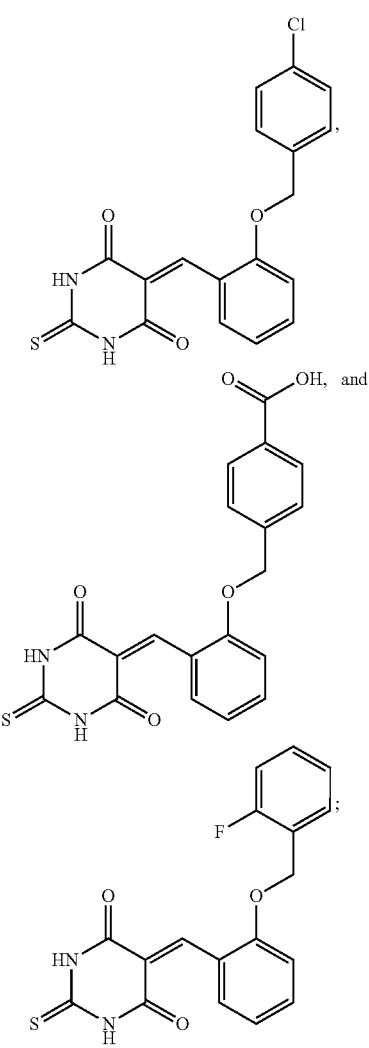

or a pharmaceutically acceptable salt thereof.

* * * * *